(12) United States Patent
Rutty et al.

(10) Patent No.: US 8,652,802 B2
(45) Date of Patent: Feb. 18, 2014

(54) SAMPLING DEVICE

(75) Inventors: Guy Nathan Rutty, Leicester (GB); Eleanor Allson May Graham, Leicester (GB); James William Strupish, Leicester (GB)

(73) Assignee: University of Leicester, Leicester, Leicestershire (GB)

( * ) Notice: Subject to any disclaimer, the term of this patent is extended or adjusted under 35 U.S.C. 154(b) by 956 days.

(21) Appl. No.: 12/670,172

(22) PCT Filed: Jul. 24, 2008

(86) PCT No.: PCT/GB2008/050620
§ 371 (c)(1),
(2), (4) Date: Jan. 22, 2010

(87) PCT Pub. No.: WO2009/013548
PCT Pub. Date: Jan. 29, 2009

(65) Prior Publication Data
US 2010/0184126 A1 Jul. 22, 2010

(30) Foreign Application Priority Data
Jul. 24, 2007 (GB) .................................. 0714351.4

(51) Int. Cl.
*G01N 1/30* (2006.01)
(52) U.S. Cl.
USPC ....................................................... 435/40.5
(58) Field of Classification Search
None
See application file for complete search history.

(56) References Cited

U.S. PATENT DOCUMENTS

| 4,735,905 | A  | * | 4/1988  | Parker ........................ 436/174 |
|-----------|----|---|---------|----------------------------------------|
| 5,467,780 | A  | * | 11/1995 | Nabai et al. .................. 600/567 |
| 6,440,373 | B1 | * | 8/2002  | Gomes et al. ................. 422/547 |
| 7,722,549 | B2 | * | 5/2010  | Nakao ......................... 600/564 |
| 7,932,099 | B2 | * | 4/2011  | Egan et al. ................... 436/514 |
| 8,187,207 | B2 | * | 5/2012  | Machold et al. .............. 600/585 |
| 2002/0139743 | A1 | * | 10/2002 | Critz et al. ................... 210/475 |
| 2003/0082797 | A1 | * | 5/2003 | Rastorgoueff et al. .... 435/309.1 |
| 2004/0260200 | A1 | * | 12/2004 | Morello ........................ 600/566 |
| 2006/0116605 | A1 | * | 6/2006 | Nakao .......................... 600/566 |
| 2007/0167957 | A1 | * | 7/2007 | Long ............................ 606/117 |
| 2007/0270710 | A1 | * | 11/2007 | Frass et al. ................... 600/567 |

FOREIGN PATENT DOCUMENTS

DE 2903760 B1 6/1980
DE 20021405 U1 3/2001

OTHER PUBLICATIONS

International Search Report for International Patent Application No. PCT/GB2008/050620 Feb. 25, 2009.

* cited by examiner

*Primary Examiner* — Ann Lam
(74) *Attorney, Agent, or Firm* — LeClairRyan, A Professional Corporation

(57) ABSTRACT

A portable sampling device (2) for obtaining a biological sample from a subject comprises sample collection means (8) for excising a biological sample (14) from a subject, and sample containment means (6) for containing excised sample (14) and sample preservative (12) for preserving excised sample. The sample collection means (8) includes sample cutting means (18) adapted, in use, to cut into the subject and release the biological sample therefrom.

11 Claims, 12 Drawing Sheets

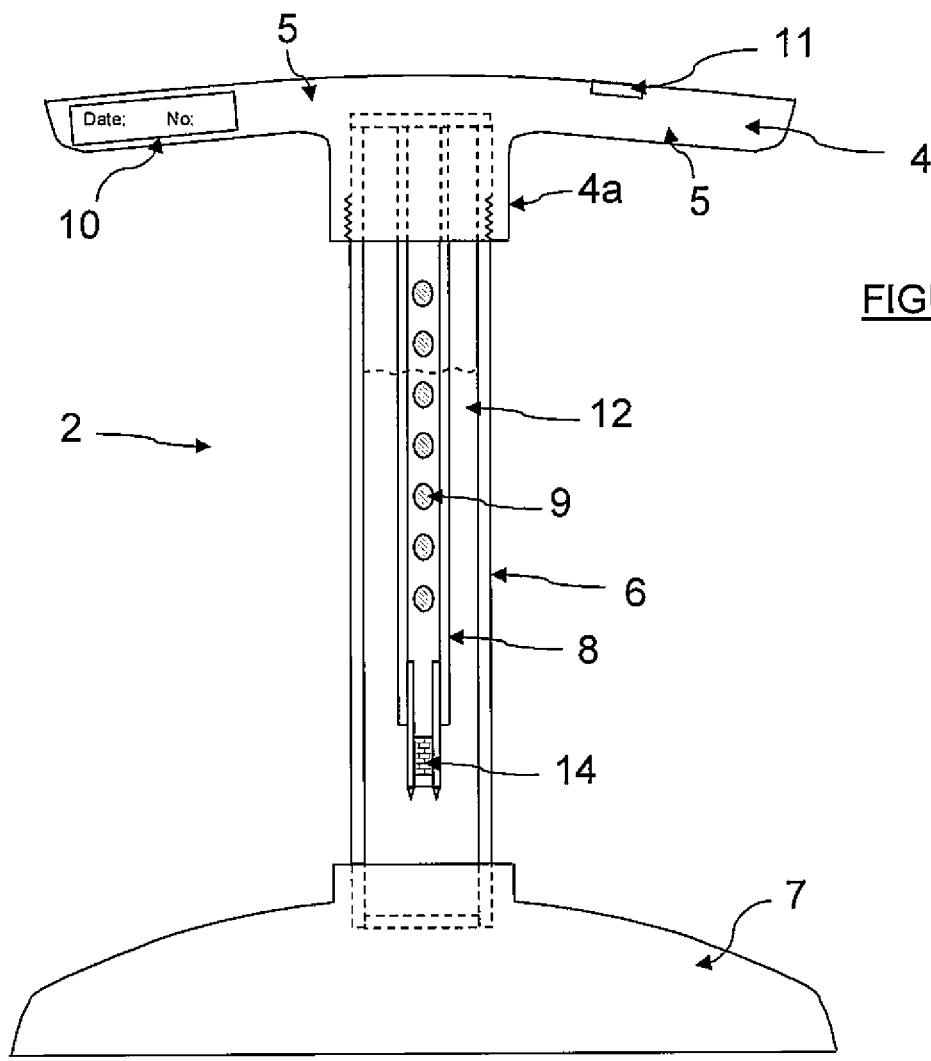
FIGURE:1

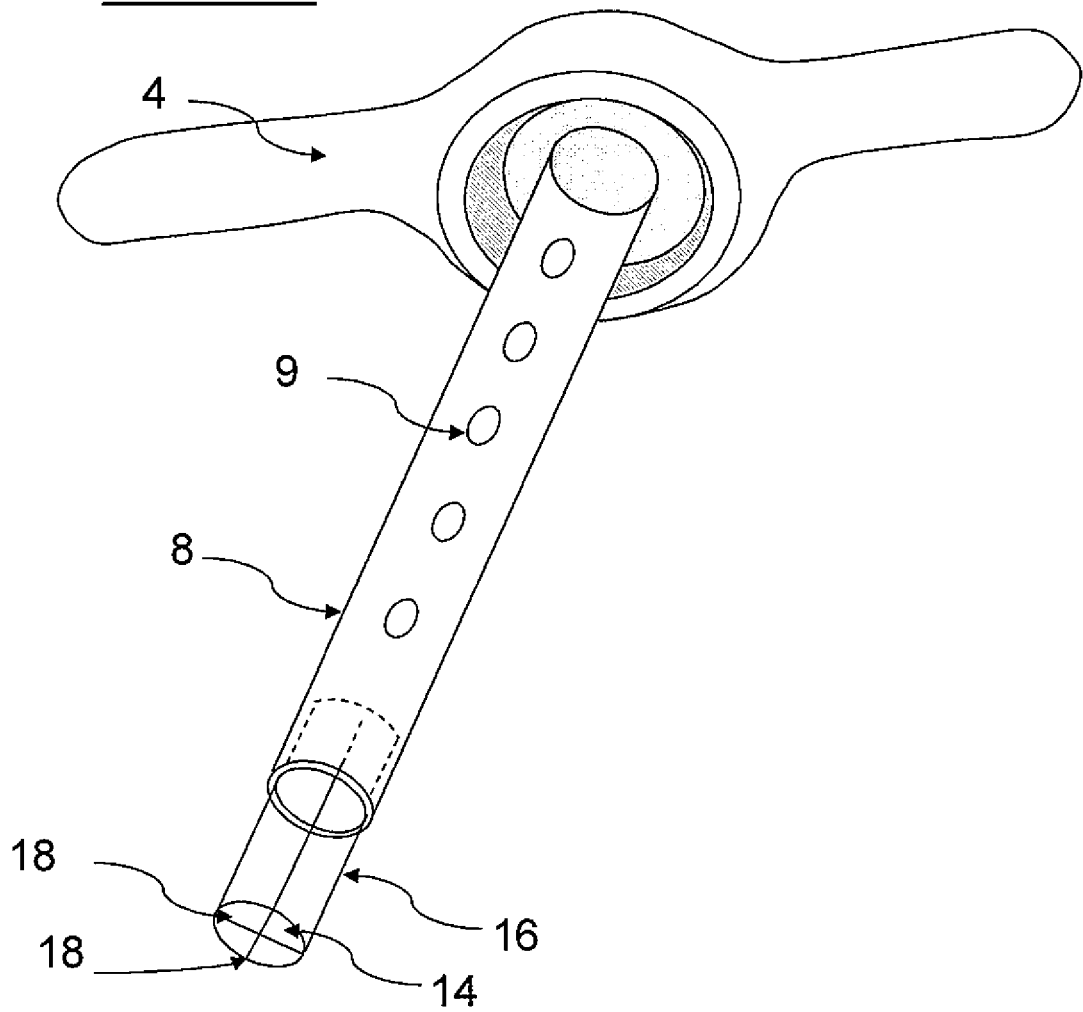

FIGURE: 3
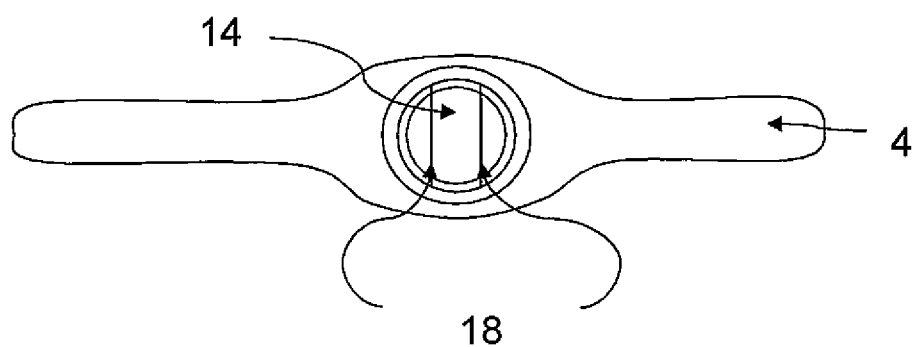
18
FIGURE: 4
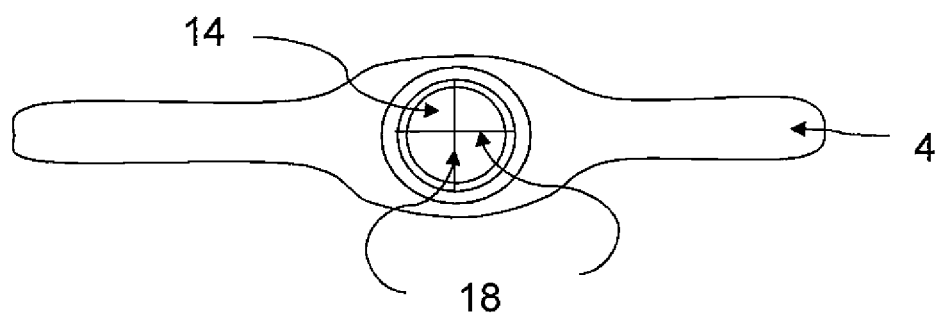
18

Figure: 5
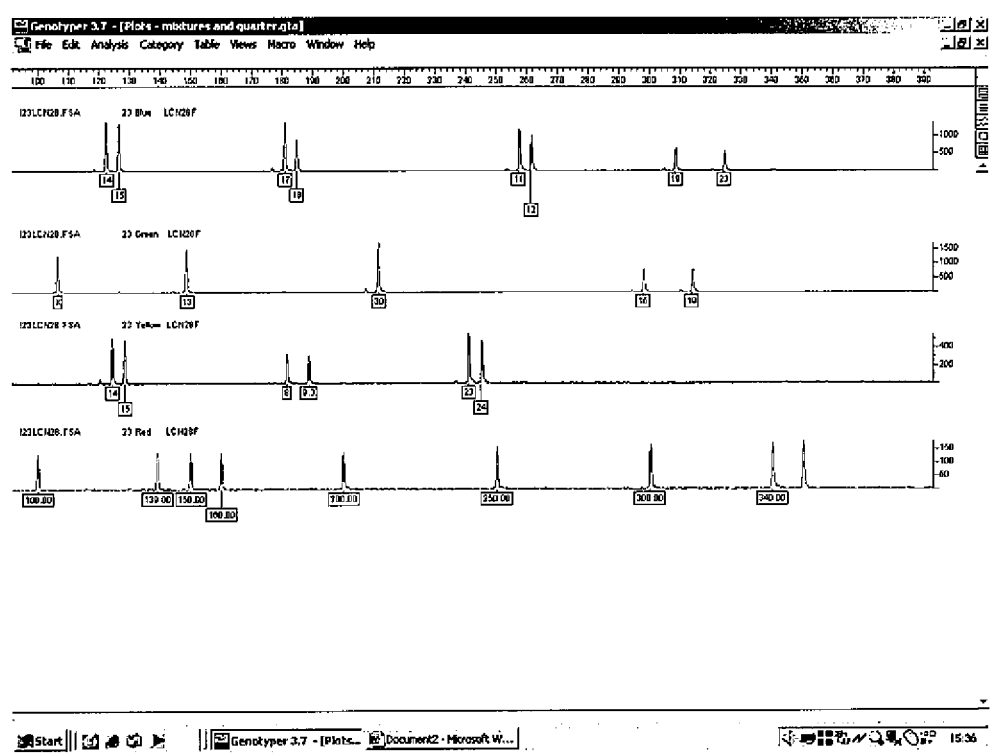

Figure: 6
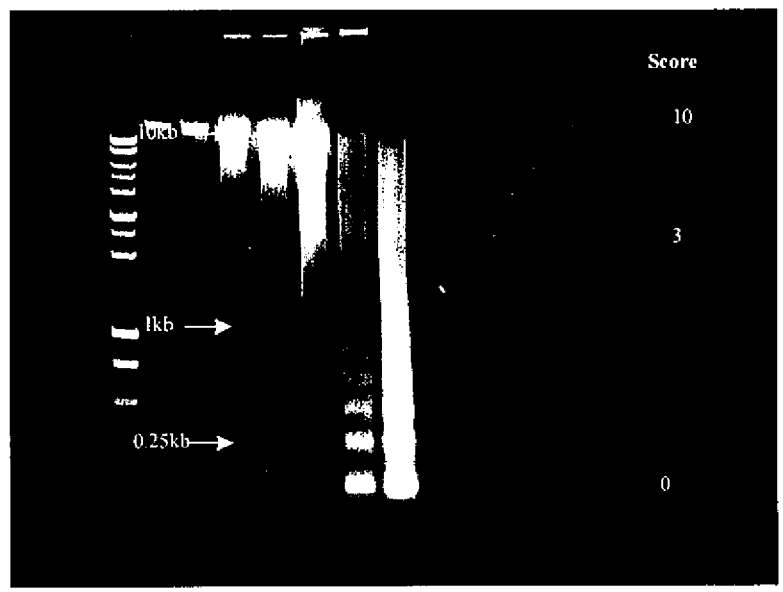
Figure: 7
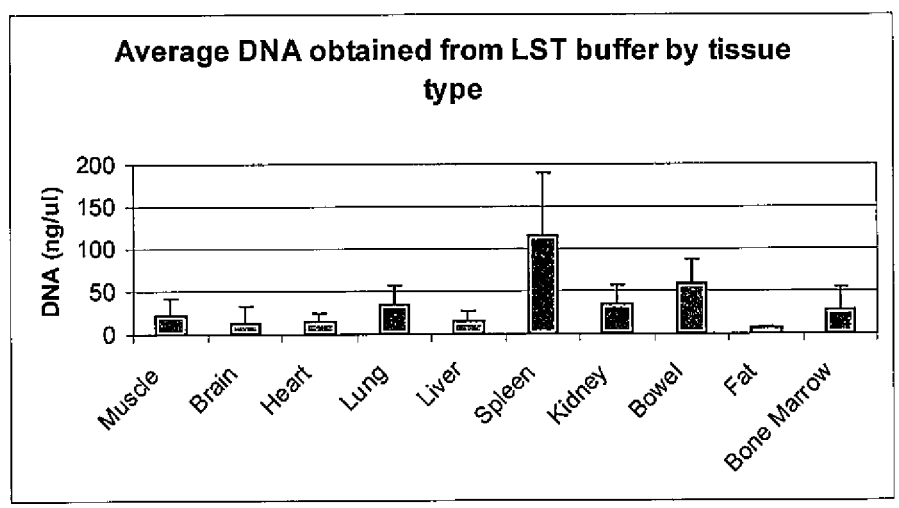

Figure: 8
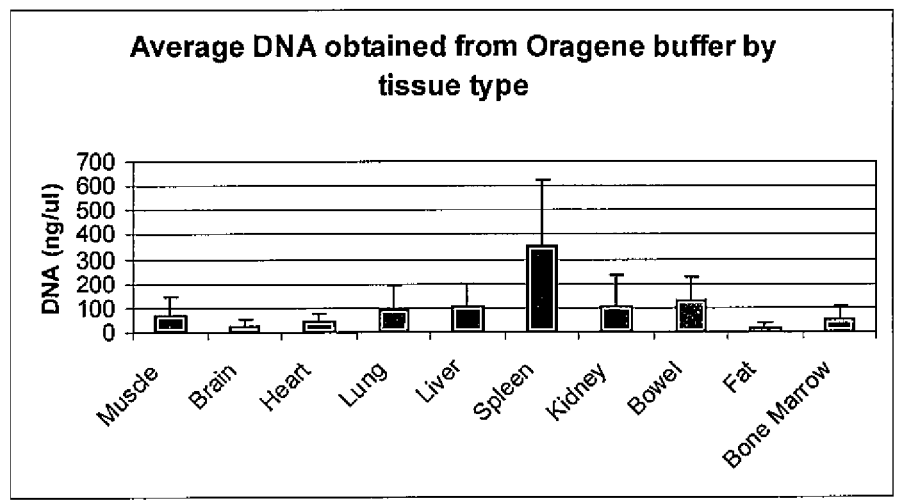
Figure: 9
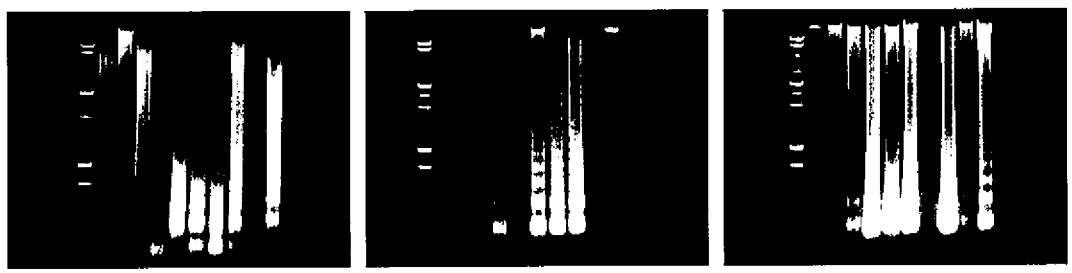

Figure: 10
a) Week 1
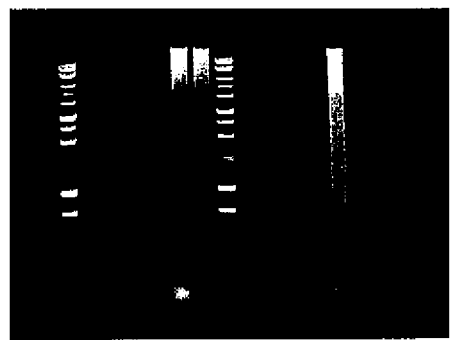
b) Week 2
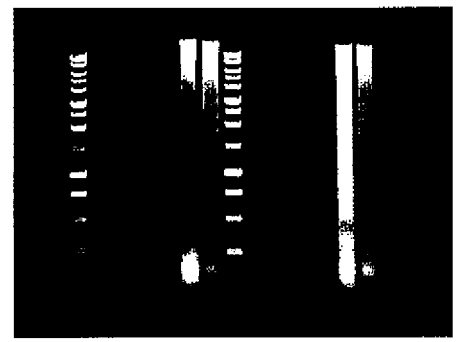
c) Week 4
d) Week 12
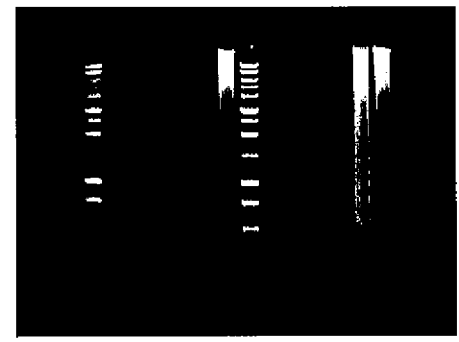
e) Week 12 frozen samples – muscle A then B
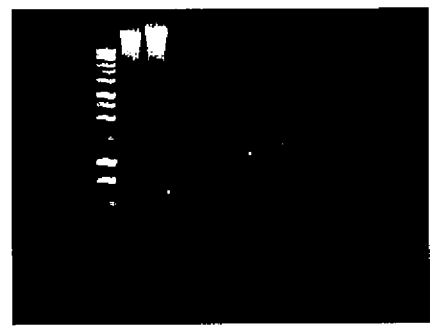

Figure: 11
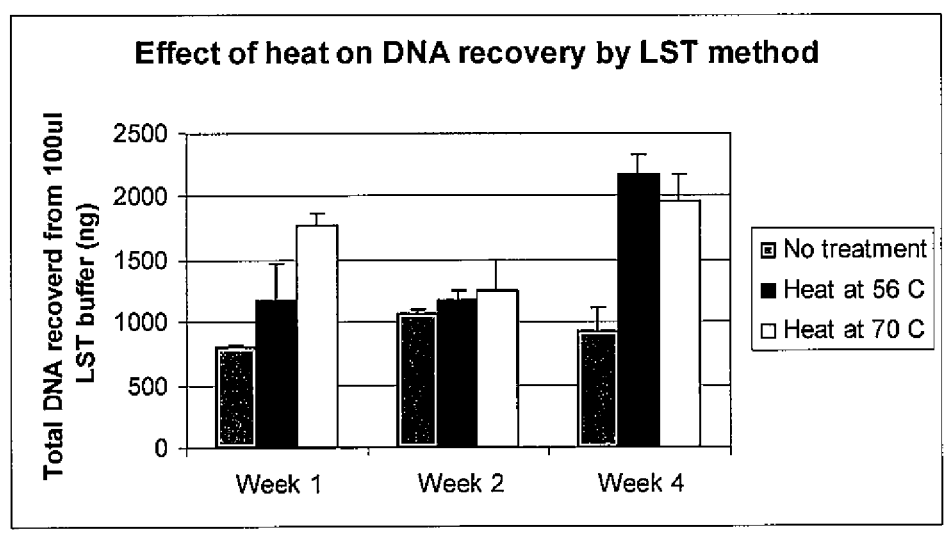

Figure: 12

| Preservative | Muscle A (mg) | Week number | | | | | | Muscle B (mg) | Week number | | | | | |
|---|---|---|---|---|---|---|---|---|---|---|---|---|---|---|
| | | 1 | 2 | 4 | 12 | 36 | 52 | | 1 | 2 | 4 | 12 | 36 | 52 |
| ORAGENE | 1000 | 33.500 | 60.430 | 33.500 | 97.100 | 111.550 | 68.950 | 1000 | 79.610 | 76.260 | 79.610 | 112.760 | 303.360 | 139.700 |
| | 500 | 46.110 | 52.840 | 46.110 | 65.730 | 67.270 | 61.670 | 500 | 27.830 | 52.600 | 27.830 | 137.930 | 161.510 | 61.570 |
| | 250 | 15.140 | 19.850 | 15.140 | 40.380 | 42.770 | 21.790 | 250 | 9.770 | 10.590 | 9.770 | 15.640 | 42.710 | 14.260 |
| | 100 | 1.890 | 6.770 | 1.890 | 4.000 | 9.090 | 5.670 | 100 | 1.630 | 1.850 | 1.630 | 2.770 | 6.460 | 2.040 |
| | 50 | 0.798 | 1.150 | 0.798 | 0.912 | 1.410 | 1.790 | 50 | 0.297 | 0.732 | 0.297 | 2.540 | 6.120 | 1.970 |
| | 25 | 0.233 | 0.523 | 0.233 | 0.626 | 3.260 | 0.458 | 25 | 0.630 | 0.877 | 0.630 | 1.160 | 2.010 | 0.609 |
| | 10 | 0.143 | 0.127 | 0.143 | 0.230 | 0.233 | 0.009** | 10 | 0.070* | 0.053 | 0.070 | 0.239 | 0.062 | 0.006** |
| | 5 | 0.039 | 0.032* | 0.039 | 0.035* | 0.012** | 0.005* | 5 | 0.156 | 0.171 | 0.156 | 0.352 | 0.111* | 0.014** |
| 5ml LST | 1000 | 0.093 | 0.179 | 0.093 | 1.580 | 0.948 | 0.047 | 1000 | 0.059 | 0.278 | 0.059 | 9.490 | 64.280 | 3.530 |
| | 500 | 0.185 | 0.248 | 0.185 | 0.512 | 3.290 | 0.289 | 500 | 0.253 | 0.276 | 0.253 | 1.340 | 6.740 | 0.983 |
| | 250 | 0.129 | 0.131 | 0.129 | 0.219 | 0.371 | 0.101* | 250 | 0.239 | 0.182 | 0.249 | 0.376 | 1.550 | 0.154 |
| | 100 | 0.096 | 0.060 | 0.096 | 0.059 | 0.190 | 0.007* | 100 | 0.072 | 0.061 | 0.072 | 0.117 | 0.330 | 0.105 |
| | 50 | 0.029 | 0.031 | 0.029 | 0.068 | 0.113 | 0.027* | 50 | 0.035 | 0.014 | 0.035 | 0.062 | 0.128 | 0.022** |
| 1ml LST | 100 | 0.270 | 0.302 | 0.270 | 0.648 | 0.766 | 2.680* | 100 | 0.432 | 0.264 | 0.432 | 3.190 | 14.690 | 12.880 |
| | 50 | 0.108 | 0.134 | 0.108 | 0.320 | 0.220 | 0.628 | 50 | 0.153 | 0.172 | 0.153 | 0.674 | 4.250 | 2.150 |
| | 25 | 0.089 | 0.100 | 0.089 | 0.145 | 0.239 | 0.218 | 25 | 0.112 | 0.089 | 0.112 | 0.083 | 1.580 | 0.855 |
| | 10 | 0.021 | 0.021* | 0.021 | 0.070 | 0.052 | 0.072 | 10 | 0.035 | 0.048 | 0.035 | 0.097 | 0.275 | 0.105 |
| | 5 | 0.000*** | 0.009* | 0.010* | 0.008* | 2.630 | 0.025* | 5 | 0.014* | 0.018* | 0.014* | 0.035* | 0.157* | 0.036 |

Figure: 13
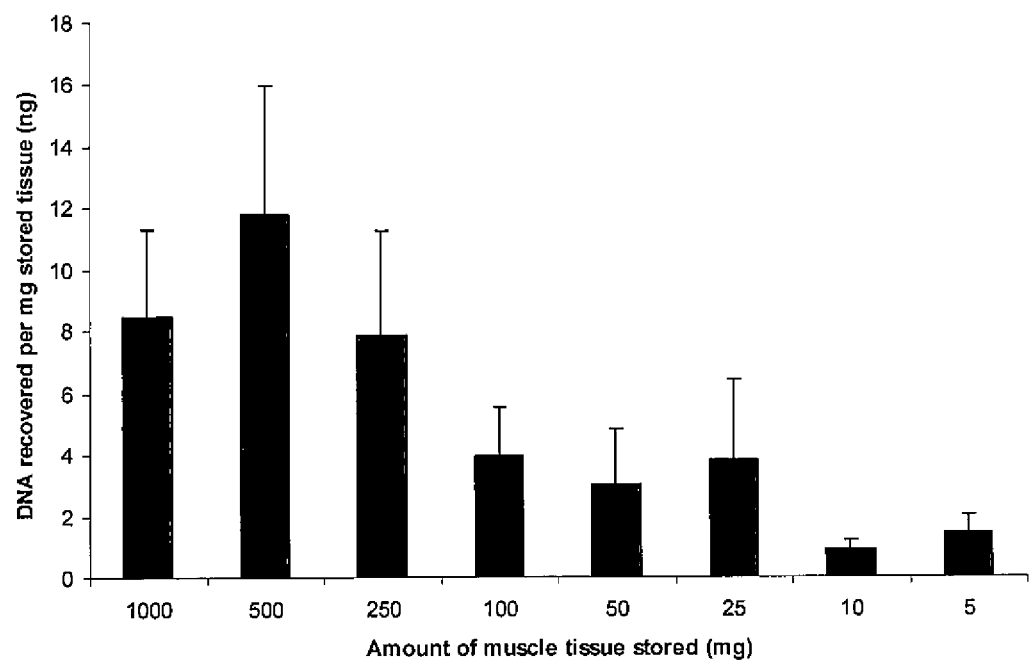

Figure: 14
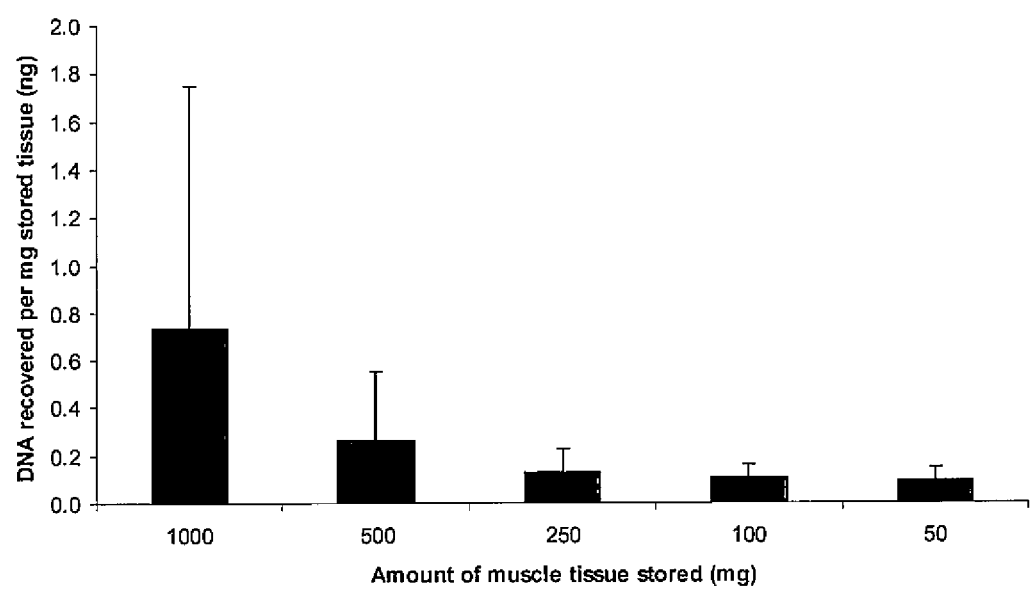

Figure: 15
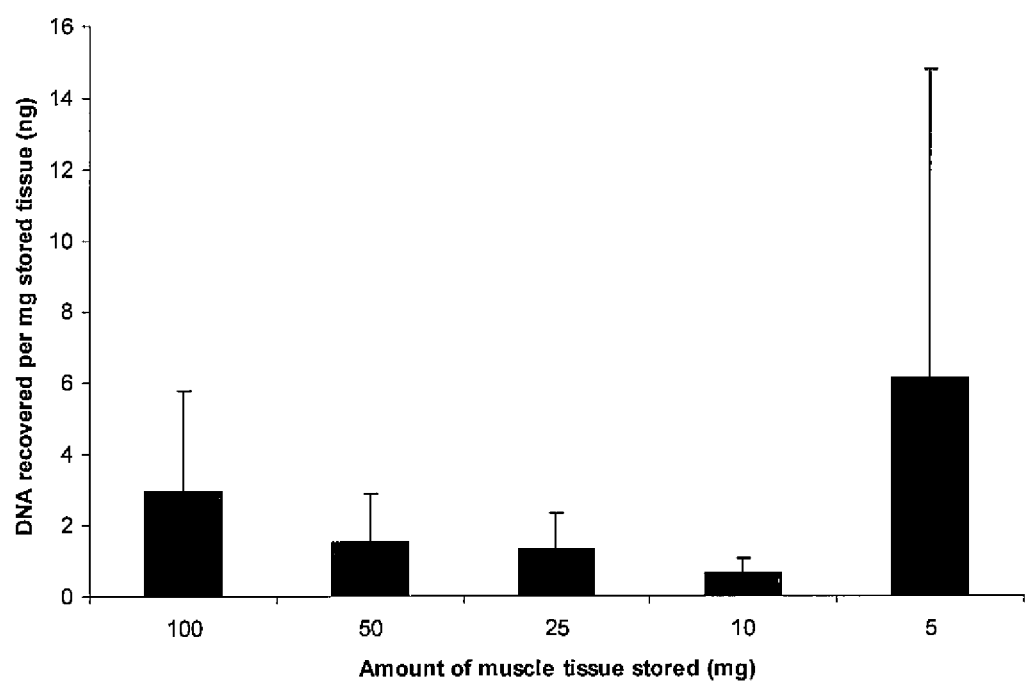

SAMPLING DEVICE

This application is a national stage application under 35 U.S.C. §371 from PCT Application No. PCT/GB2008/050620, filed Jul. 24, 2008, which claims the priority benefit of Great Britain Application No. 0714351.4, filed Jul. 24, 2007.

The present invention relates to sampling devices, and particularly, to sampling devices for obtaining a biological sample from a subject. The invention extends to methods for obtaining a biological sample, such as a tissue sample, from a subject, and to methods for preserving the sample for subsequent analysis, such as for genetic identification purposes.

Today, both in the living and the dead, the use of human genomic DNA is an established method for human identification. In normal, non-contaminated circumstances, be it for single or multiple fatalities, DNA analysis is used as a primary technique for the identification of the dead, as well as the re-association of disrupted body parts. Recovery of suitable samples for subsequent DNA analysis may be undertaken in the mortuary by a pathologist. The choice of sample that is taken is dependent upon the general state of the remains; the more decomposed or disrupted the body, the more difficult the decision becomes. The samples are placed in a suitable storage medium, which is then refrigerated or frozen for future examination. The extraction, amplification and analysis of the sample are undertaken at laboratories using commercially available kits and genetic analysers. The DNA profile of the test sample is usually compared to national DNA databases or samples taken from relatives or personal possessions of the suspected deceased individual.

Tissue preservation is also a critical issue in forensic investigations where human remains are collected for DNA analysis following a Chemical, Biological, Radiological or Nuclear (CBRN) incident, or a disaster, such as after a plane crash, terrorist bombing, homicide, or mass murder. Low ambient temperatures and rapid recovery of human remains are ideal conditions to ensure successful DNA analysis of human remains. However, such conditions are difficult to achieve in disaster areas, or in geographically remote regions of the world.

Unlike a traditional non-contaminated mass fatality incident, a CBRN incident will pose problems with the recovery and use of DNA for identification purposes. Such problems include the fact that, if the identification process is carried out either where the dead body lies, ie the "hot zone", it would need to be decided if DNA samples were required for the identification process, which samples to take, how they should be stored, and also where they will be analysed. Furthermore, in the case of disrupted body parts, a policy decision would need to be made as to the minimal size of any single body part from which the DNA sample should be taken for identification and re-association purposes. In addition, the person taking the biological sample from the deceased would be required to wear gloves, which results in a significant loss in dexterity and sensitivity while taking the sample, and this makes the act of sampling even more difficult.

Further problems encountered when taking a tissue sample after a CBRN incident are that the sample, and hence DNA therein, may be contaminated after it has been recovered from the body, especially if the body is itself contaminated. This can often be the case when an external sample is biopsied from the exterior of the subject, for example, by scraping, crushing or punching out a sample from the subject. Furthermore, in cases where the sample has to leave the "hot zone" for subsequent analysis, the laboratory and equipment where the analysis is undertaken may also become contaminated.

In addition, a CBRN incident could be due to terrorist activity. Thus, not only would there be an issue of identification of the dead, but there would also be issues related to the police criminal investigation and the search for terrorists and additional potential terrorists. DNA has a role in suspect identification and thus samples may also arise related to the investigation of DNA contamination of, for example, bomb components through handling or oral contamination. This will lead to a conflict of interest between the safe handling of the bodies and the investigation of the crime.

In view of the foregoing, it will be appreciated that there is an ongoing need for improved tissue sampling devices, which may be used to extract a sample of tissue and hence DNA from the body of a subject, which may then be subsequently genetically profiled in order to identify the subject.

The system should be able to be used on whole or disrupted bodies, at the scene or in the identification process or temporary mortuary. It must be safe to use in CBRN personal protective equipment (PPE) and require minimal training which may have to occur on-site immediately prior to use.

The use of blood samples is problematic in that blood is not always easy to acquire, especially from a disrupted body. The inventors also wanted to avoid the use of small bore surgical needles to reduce the possibility of needle stick injuries. The inventors also considered the use of cotton wool swabs pushed into muscle or solid organs as had been done in the aftermath of the Asian Tsunami in 2004 but that approach would not yield sufficient high quality DNA for analysis.

It was also desired to develop a system that requires only very tiny amounts of tissue, in contrast to the present sampling regimes for DNA from cadavers where pathologists may be encouraged to take tens of grams of tissue for DNA identification purposes.

Therefore, it is an object of the present invention to overcome or mitigate one or more of the problems of the prior art, whether identified herein or elsewhere, and to provide a tissue sampling device for the collection of biological samples from a subject that could be used with whole bodies or body parts, either at a scene of death or in a mortuary, and which could utilise the available tissue with one sampling system. While the device may be used following a CBRN incident, it should also be applicable to any death investigation, be it a single or mass fatality incident, whole or disrupted bodies, contaminated or non-contaminated. It is important that the sampling device is universally applicable to as many types of tissue samples as possible. Furthermore, it is desirable that the device can be used to collect a sample from within (ie inside) the subject in order to avoid the possibility of surface contamination which could be introduced if the collection method was dependent on crushing or punching out the sample from the subject.

Hence, according to a first aspect of the invention, there is provided a portable sampling device for obtaining a biological sample from a subject, the device comprising sample collection means for excising a biological sample from a subject, sample containment means for containing excised sample and sample preservative for preserving excised sample, wherein the sample collection means comprises sample cutting means adapted, in use, to cut into the subject and release the biological sample therefrom.

The sampling device according to the first aspect of the invention may be used to quickly and easily carry out a biopsy from a subject in order to obtain a biological sample therefrom. Once the sample has been biopsied from the subject by the cutting means, and stored in the containment means, the device may then be removed from the subject, and the sample may be subsequently analysed. Analysis may be either on site (ie in the hot zone) or in a remote laboratory. Advantageously, the sample preservative ensures that the excised sample is preserved at ambient or room temperature until such a time that it is analysed. Accordingly, there is no need for a refrigerator or freezer or any other sample preservation devices when using the device according to the invention.

Furthermore, the sample preservative maintains the integrity of nucleic acid (eg DNA) within the sample for longer periods than would otherwise be possible, which is useful particularly during the stress and demands of a mass disaster or other related event. In addition, the sampling device has no requirement for an external power source or additional machinery to operate. Hence, the device according to the invention provides significant benefits for the forensic community, because it is convenient to use, enabling quick sample collection and preservation in an ambient temperature environment.

The sampling device is hand-held, and so may be operated by a single operator. The device is easily portable, and compact to the extent that it can be mailed anywhere in the world where required at very short notice. Hence, the device may be used in any environment (including those contaminated by chemical, biological or radiological substances), where an operator can enter either with or without the need for personal protective equipment, and whether oxygen is present or not. Hence, the device according to the first aspect may even be used in an oxygen deficient atmosphere as long as the operator is wearing a self-contained breathing apparatus. Alternatively, the device may be used by a suitable robotic system in environments where a human cannot obtain such a sample.

The sample collection means preferably comprises closure means which is adapted to sealingly engage with the sample containment means. Preferably, the closure means is attached to or integral with the sample collection means. Hence, when the closure means is in sealing engagement with the containment means, the sample collection means is contained inside the containment means. Preferably, the preservative is contained within the containment means. Hence, when the closure means is sealed with the containment means, leakage of preservative is prevented.

Thus, according to a more specific aspect of the invention, there is provided a portable sampling device for obtaining a biological sample from a subject, the device comprising sample collection means for excising a biological sample from a subject, sample containment means for containing excised sample and sample preservative for preserving excised sample, wherein the sample collection means comprises sample cutting means adapted, in use, to cut into the subject and release the biological sample therefrom, and wherein the sample collection means comprises a closure adapted to engage with and seal the sample containment means.

Preferably, the sample collection means is adapted, in use, to excise the biological sample from the interior of the subject.

By the expression "excise a sample from the interior of the subject", we mean that the sample that is obtained from the subject is an internal sample as opposed to an external sample which would be taken from the outside of (ie the external surface) the subject. Use of internal samples significantly minimises the risk of surface contamination which could be introduced if the collection method was dependent on crushing or punching out the sample from the subject. Accordingly, the sample collection means ensures that the amount of any external regions of the subject that are excised are minimized.

Preferably, the sample collection means is suitably shaped such that it may be inserted into the subject such that the cutting means can cut out an internal sample therefrom. It is preferred that the sample collection means is substantially elongate. Preferably, the sample collection means is at least 2 cm in length, more preferably at least 3 cm in length, and most preferably at least 4 cm in length. The sample collection means may be up to about 10 cm in length. Preferably, the sample collection means is between about 2 cm and 10 cm, or between about 4 cm and 10 cm, eg about 5 cm and 6 cm, in length.

Preferably, the sample collection means is substantially tubular in shape. The sample collection means may therefore comprise a tube. Preferably, the sample collection means is cylindrical. Preferably, the sample collection means has a substantially circular cross-section. The diameter of the collection means may be at least 2 mm, more preferably at least 3 mm, even more preferably at least 4 mm, and most preferably at least 5 mm. The diameter of the collection means may be up to about 1 cm in diameter. Preferably, the diameter of the collection means is between about 2 mm and 10 mm, more preferably between about 5 mm and 10 mm, eg about 6 mm and 8 mm.

Preferably, an end of the sample collection means that is distal from the closure means is sufficiently sharp such that it is capable of cutting into the subject. The sample collection means may be made of plastic or metal, or a composite thereof. For example, the distal end of the collection means may be made of metal and the rest of the collection means may be made of plastic. It is preferred that the entire collection means is made of plastic or a polymer. Preferably, the sample collection means comprises an opening at or near the distal end, which opening leads to a space in which excised sample may be retained. Preferably, the sample collection means comprises a channel or lumen extending therethrough. The channel is preferably connected to the opening at or near the distal end of the collection means.

Preferably, the cutting means is disposed at, or may be, the distal end of the collection means. The sample cutting means preferably comprises a single cutting point or edge which contacts the subject to excise the sample therefrom. Preferably, the cutting means is adapted, in use, to contact and cut into only one side of the subject. Preferably, in use, a cutting force is applied to the subject via the cutting means against only one side of the subject, preferably substantially along a single plane. The distal end may be sharpened such that it is adapted to cut into the subject thereby releasing a sample from within. The cutting means may be flat or beveled.

Preferably, the sample collection means incorporates a closure that is engageable with the sample containment means in such a way that the sample collection means is disposed within the sample containment means. Thus, a sample held within the sample collection means may be immersed in a preservative solution within the sample containment means.

For example, the sample collection means may comprise a punch. Preferably, the punch has an opening in its tip which leads to a channel which extends at least partially through the punch. Advantageously, the use of a single punch is a very simple mechanism by which the sample may be extracted from the subject.

Preferably, the cutting means comprises at least one cutting member extending across the distal end of the sample collection means, and most preferably across the opening in or near the end thereof. Preferably, the cutting means comprises at least two cutting members extending across the distal end of the sample collection means, and most preferably, across the opening in or towards the end thereof. The cutting members may be spaced apart from each other. The cutting member may be substantially parallel with each other. However, it is preferred that the cutting members may cross over each other. For example, the cutting members may form a cross in the distal end of the sample collection means, and most preferably, across the opening in or near the end thereof. Preferably, the cross formed by the cutting members is substantially centrally disposed in the distal end of the collection means. It is envisaged that more than two cutting members may be provided in the distal end of the sample collection means. However, it will be appreciated that not so many cutting members are provided such that the opening in the end of the collection means becomes effectively blocked so that an excised sample cannot enter the channel in the collection means.

The or each cutting member may be a wire. The wire preferably has a diameter that is sufficiently small so that it can cut into the subject to release a sample therefrom. The cutting means may be attached to the sample collection means by welding. Advantageously, the cutting wires cut a first end of the sample as the punch is pushed into the subject, and also a second end of the sample as the punch is pulled away from the subject. However, the cutting wires not only serve the purpose of cutting into the subject and for separating the sample therefrom. Therefore, preferably, the sample cutting means is adapted to retain the excised sample in the sample collection means. Both arrangements of cutting wires in the end of the collection means have been tested and found to be effective at cutting a tissue sample out of the subject. However, the embodiment shown in FIG. 4, in which the wires form a cross, is believed to be more effective because the cross shape is surprisingly effective at retaining excised sample in the collection means.

Hence, advantageously, the cutting means retains the sample inside the hollow lumen of the punch thereby preventing it from falling out. This arrangement therefore is far better than use of a manual or electrical suction device, forceps, screw, sleeve or basket or the like.

The cutting means is used to cut out a sample of internal soft tissue from the subject, and this minimizes the risk of contamination by non-subject DNA containing material that may be present on the surface of the area on the subject being sampled. Preferably, and advantageously, the cutting means is operable in use to cut into the subject from a single direction so that it can be used on any depth of tissue for sample collection. This is particularly advantageous in the collection of soft tissue samples from a subject, for example, for disaster victim identification, as it allows collection from whole or fragmented corpses.

Furthermore, the cutting means enables the collection of a tissue sample even when access to the subject is only possible from one direction or plane, and where the available sampling site of the subject is thick. Hence, the device according to the invention is not limited solely to retrieving samples from thin accessible areas, such as the ear or the webbing between fingers or toes.

Once the sample has been excised from the subject, the closure means and the sample collection means is engaged with the containment means, and tightly sealed thereto, such that the sample preservative cannot not leak therefrom. The sample retained in the distal end of the collection means is now immersed in the preservative so that nucleic acid (such as nuclear DNA or mitochondrial DNA or RNA) in the sample is preserved for subsequent analysis. It will be appreciated that it is important that the nucleic acid in the sample is fully preserved to facilitate the nucleic acid analysis conducted thereon, and to ultimately improve the speed and accuracy of the subsequent identification analyses.

Hence, preferably, the sample collection means comprises at least one opening, and preferably a plurality of openings, through which preservative may flow into the sample collection means. The at least one opening allows the preservative solution to pass from the containment means to the inside of the collection means such that it contacts and ultimately soaks the excised sample, not only from the outside of the containment means (ie through the opening in the distal end thereof), but also from inside the collection means. Hence, both ends of the sample are contacted with preservative, thereby improving the preservation of the sample inside the collection means. Preferably, the at least one opening is provided at or near the distal end of the sample collection means. Preferably, the openings are spaced apart and disposed along a longitudinal axis of the sample collection means. Furthermore, preferably, the openings are spaced apart and disposed around the circumference of the collection means. For example, there may be openings on diametrically opposing sides of the sample collection means, spaced along the longitudinal axis thereof. Preferably, the sample collection means is perforated.

Preferably, the at least one opening is not so large that the excised sample can pass therethrough. Accordingly, preferably, the at least one opening in the side of the collection means is smaller in diameter than the opening in the distal end of the collection means through which the sample enters the collection means.

Particularly preferred embodiments of the invention therefore comprise a sample container and a closure assembly, the closure assembly incorporating the sample collection means, which sample collection means has the form of an open-ended punch with an axial lumen. The arrangement is such that when the closure assembly is engaged with the sample container, the punch is disposed within the sample container. The punch is provided with at least one lateral opening via which sample preservative can pass into the lumen of the punch and hence come into contact with a sample held in that lumen.

The sample preservative for preserving the sample is preferably fluid. As shown in FIG. 1, the containment means is preferably filled with a solution of preservative, which is provided to preserve the sample after it has been biopsied from the subject until such time that it is analysed.

By the terms "preservative" or "preserving", we mean a composition capable of inhibiting or preventing damage, spoilage or decay of the sample whether from microbial growth, or undesirable chemical changes.

Preferably, nucleic acid profiling is carried out on the sample. Hence, it is preferred that the preservative is adapted to prevent or inhibit damage to nucleic acid present within the sample, and most preferably nucleic acid, such as nuclear DNA or mitochondrial DNA or RNA. The preservative may be a natural or synthetic chemical. The preservative preferably has a long shelf-life both before use and after use, ie with the sample in it. The shelf-life of the preservative may be at least one month, and preferably, two, three or four months. Preferably, the shelf-life is at least six months, more preferably at least twelve months. Most preferably, the shelf-life of the preservative is at least two, three, four or five years.

Preferably, the preservative comprises a first component for preserving the sample, and preferably the nucleic acid in the sample, without the need for it to be refrigerated or frozen. The sample may therefore be stored at room temperature, thus allowing the device to be stored and used anywhere in the world in any environment without the need for freezing or even refrigeration of the sample. For example, the first component may comprise potassium chloride (KCl).

Preferably, the preservative comprises a second component adapted to at least initiate nucleic acid extraction from the sample upon contacting therewith. This second component speeds up the nucleic acid analysis process, making it possible to undertake on-scene nucleic (eg DNA) analysis. This reduces the need to handle or dissect the sample in the laboratory, thereby avoiding risk of sample contamination. Preferably, the second component is capable of lysing cells and deactivating nucleases, thereby speeding up the downstream processing of the sample and aiding sample preservation. For example, the second component may comprise a detergent. Examples of suitable detergents include Nonidet P40 or Tween 20.

Preferably, the preservative comprises a third component adapted to decontaminate the sample thereby improving storage thereof. This can be achieved for biological contaminants by use of an anti-microbial agent as these do not interfere with the processes involved in DNA profiling. For example, the third component may comprise sodium azide. Preferably, the preservative is compatible with DNA profiling techniques using commercially available systems, or lab-on-a-chip technology.

Two preferred embodiments of preservative designed for room temperature preservation of field-collected samples were investigated. The first embodiment, referred to herein as Solution A, preferably comprises Oragene DNA Self-Collection kit from DNA Genotek, Ottawa, Ontario, Canada. The second embodiment of preservation solution, referred to herein as Solution B (LST buffer), preferably comprises 100 mM Tris-HCl (pH 8.3); 0.5M KCl; 4.5% Nonidet P40; 4.5% Tween 20; and 1% Sodium Azide.

It will be appreciated that the preservative used within the sampling device is not limited to the two described herein, but may also be any other buffer or solution available to perform the same preservative function, or any buffer or solutions that becomes available for this purpose. It will also be appreciated that the sample preservative is a complete buffer solution that does not require any separation from the sample collection means or cutting means in order to remain active.

The sampling device may be supplied with a quantity of preservative held within the sample containment means. Alternatively, the sample containment means may be charged with a quantity of preservative prior to use.

The device may comprise anti-tamper means for inhibiting opening of the device once a sample is within the containment means. The closure means may comprise a removable seal associated with the closure means and/or containment means to ensure that the device has not been tampered with prior to use. The device may comprise identification means by which the sample may be easily identified. For example, the identification means may comprise a radio frequency identification device (RFID) for labelling and tracking of the sample. The identification means preferably comprises a label on which a barcode and other information about the sample may be placed, for example, site and date of sampling.

Preferably, the biological sample taken from the subject comprises biological tissue. Hence, the device may be considered to be a biopsy device. The sample is preferably an internal sample from the subject, ie not on the surface or outside of the subject. Use of internal samples minimises the risk of collecting material which contains contaminating non-subject nucleic acid. The device is preferably used for the purposes of nucleic acid profiling. Hence, the biological sample preferably comprises nucleic acid, and preferably DNA. The device is preferably used for the collection and preservation of nucleic acid within a soft or wet tissue sample. Preferably, and advantageously, the device does not itself require the use of any nucleic acid, only the nucleic acid provided in the sample. Hence, an operator can be confident that the results of any genetic analyses conducted on the sample will be derived from DNA from the sample as opposed to elsewhere. Furthermore, the device is single use as opposed to multiuse, and this improves the confidence associated with DNA profiling results obtained.

It will be appreciated that the device may be used to extract a biological sample from any sample. The device may be used to extract a biological sample from any substance of solid to semi-solid consistency, but generally not hard materials or liquids.

For example, the subject may comprise plant matter, such as fruit or vegetable matter. The subject may comprise a foodstuff, for example, meat, cheese, fish, dairy products, bread, pastries or confectionery.

The subject may be non-human, for example an animal. The device can be used on any human or non-human subject, for example any large or small breed, domestic, wild or farmed animal in captivity or in the wild. The animal may be a livestock animal, such as a horse, cow or sheep. However, the subject is preferably human.

It is especially preferred that the device according to the first aspect of the invention is used for the collection of a nucleic acid sample from either a whole body or a body part, for example, at a scene of death or in a mortuary. The device is preferably used following a Chemical, Biological, Radiological or Nuclear (CBRN) incident, but may be applicable to any death investigation, be it a single or mass fatality incident, on whole or disrupted bodies, which may or may not be contaminated.

Hence, it is preferred that the subject from which the sample is collected is dead.

According to a second aspect of the invention, there is provided use of the sampling device according to the first aspect for obtaining a biological sample from a subject.

In a third aspect, there is provided a method for obtaining a biological sample from a subject, the method comprising the steps of:—
a) contacting sampling collection means of the device according to the first aspect with a subject such that cutting means cuts into the subject;
b) withdrawing the sample collection means from the subject such that a biological sample is excised from the subject; and
c) inserting the sample collection means into sample containment means, such that the excised sample is preserved by sample preservative.

The use of the second aspect and method of the third aspect may be carried out directly on the subject, which is preferably dead. Preferably, the subject is a whole human or a part thereof. Preferably, the biological sample comprises solid or semi-solid tissue. The biological sample preferably comprises soft tissue. Suitable soft tissue includes tissue obtainable from any organ, but most preferably an internal organ. Examples of suitable sampling sites include without limitation intestine, stomach, muscle, brain, heart, lung, liver, spleen, kidney, bowel, fat, connective tissue, or bone marrow. An example of suitable semi-solid tissue from which the sample may be taken is faeces. Hence, for example, the device may be used to collect a sample of dog faeces for subsequent genetic profiling.

It is preferred that the biological sample is not fluid, such as blood or lymph, and not solid tissue, such as bone or teeth.

In the use according to the second aspect, or the method according to the third aspect, an operator must first remove the closure means from the containment means in which approximately 10 ml-20 ml of sample preservative (eg solution A or B) is contained. The method preferably comprises contacting the distal end of the sample collection means with the subject at the point of intended biopsy, ie from where the tissue sample is to be extracted from the subject. Generally, the tissue sample is a small piece of soft tissue, such as muscle, and so the sample collection means is preferably contacted therewith.

Preferably, the method comprises pushing down on to the closure means, thereby urging the cutting means into the subject such that the cutting wires are urged into and cut into the subject. In so doing, a sample is cut out of the subject, which is preferably urged into the hollow lumen of the collection means. The method preferably comprises pushing the closure means towards, and hence the cutting means into, the subject adequately to ensure that a sample of sufficient size (eg about 1 cm in length, and about 4 mm in diameter) has been cut out of the subject. The method preferably comprises withdrawing the device from the subject such that the cutting means cut the sample so that is free to be pulled out of the subject for storage purposes. The method may comprise rotating or twisting the closure means, and hence the cutting means, to improve cutting of the sample. This facilitates sample removal from the subject.

The amount of biological sample excised by the sample collecting means may be from about 10 mg to about 1000 mg, preferably about 20 mg to about 750 mg, more preferably about 30 mg to about 500 mg, and most preferably about 50 mg to about 250 mg. The inventors have surprisingly found that such small amounts of sample provide sufficient nucleic acid for analysis purposes.

Preferably, the method comprises engaging the closure means with the containment means to thereby store the excised sample in the preservative therein. The excised sample may be analysed by any technique that involves the analysis of nucleic acid therein, such as nuclear DNA or mitochondrial DNA or RNA analysis. Hence, the method may comprise a step of analysing the excised sample, which may involve the use of commonly available genetic analysis techniques, such as PCR. This could involve the use of DNA sequencing, DNA profiling, SNP analysis, real time PCR, microarrays or any other technique available to analyse DNA or RNA.

In a fourth aspect, there is provided a kit for analysing nucleic acid in a biological sample, the kit comprising the sampling device according to the first aspect, and means for analysing nucleic acid present in a biological sample obtained using the device.

Suitable means for analysing nucleic acid in the sample will be known to those skilled in the art, but may include oligonucleotides required for use in nucleic acid analytical techniques, for example, PCR primers.

In summary, the device according to the invention requires sufficient downwards pressure on to the subject to ensure that the chosen tissue is cut by the cutting means, which may be rotated to sever the sample from the subject. Advantageously, the device does not require the use of any additional mechanical or electrical equipment in order for a sample to be excised and removed from the selected sample site. This is a major advantage in the device of the invention, enabling its use in situations where power sources for suction machinery may not be available. Hence, it will be appreciated that the device disclosed herein is a combined sample collection and preservation tool, designed for single usage, without the requirement of any additional mechanical, electrical or visual assistance.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 is a side view of a tissue sampling device according to the invention, partially in section and showing hidden detail;

FIG. 2 is a perspective view of a sample collector forming part of the device shown in FIG. 1;

FIG. 3 is an end view of a first embodiment of a sample collector of the general type shown in FIG. 2;

FIG. 4 is a view similar to FIG. 3, of a second embodiment of the sample collector;

FIG. 5 shows an example of a full second generation multiplex (SGM) plus profile;

FIG. 6 shows an electrophoresis gel of an example of the DNA scoring system used as described in Experiment 2;

FIG. 7 is a bar chart showing the average amount of DNA obtained from LST buffer by tissue type in Experiment 3;

FIG. 8 is a bar chart showing the average amount of DNA obtained from Oragene buffer (solution A) by tissue type in Experiment 3;

FIG. 9 shows gel electrophoresis of the DNA obtained in Experiment 3 for −20° C. storage (left gel); LST buffer (middle gel) and Oragene buffer (right gel);

FIG. 10 shows gel electrophoresis of DNA from muscle A and B sampled over a 12 week period in Experiment 4;

FIG. 11 is a bar chart showing the effect of heat (56° C. and 70° C.) on DNA recovery by LST method;

FIG. 12 is a table showing the average result of Real-Time PCR quantification performed in duplicate for all samples extracted during a 52 week time period. All results are expressed as the concentration of DNA in nanograms per microlitre. Results followed by (*) indicate samples from which a partial DNA profile was observed, and () for which DNA profiling failed after amplification at 28 cycles. A full DNA profile was obtained when all partial and failed samples were re-amplified for 34 cycles, with the exception of 5 mg muscle A stored in Oragene solution for 1 week (*), for which no DNA profile could be generated;

FIG. 13 is a bar chart to illustrate the quantity of DNA recovered from muscle tissue stored in Oragene solution. Each bar represents the average quantity of DNA recovered from a 100 μl aliquot of Oragene solution over the 6 time periods sampled. The concentration of DNA was normalised by dividing the total quantity of DNA recovered (ng) by the amount of tissue stored (mg) in each sample in order to compare the efficiency of each extraction. The error bars indicate the 95% confidence interval for each data set;

FIG. 14 is a bar chart to illustrate the quantity of DNA recovered from muscle tissue stored in 5 ml LST buffer. Each bar represents the average quantity of DNA recovered from a 100 μl aliquot of Oragene solution over the 6 time periods sampled. The concentration of DNA was normalised by dividing the total quantity of DNA recovered (ng) by the amount of tissue stored (mg) in each sample in order to compare the efficiency of each extraction. The error bars indicate the 95% confidence interval for each data set; and FIG. 15 is a bar chart to illustrate the quantity of DNA recovered from muscle tissue stored in 1 ml LST buffer. Each bar represents the average quantity of DNA recovered from a 100 μl aliquot of Oragene solution over the 6 time periods sampled. The concentration of DNA was normalised by dividing the total quantity of DNA recovered (ng) by the amount of tissue stored (mg) in each sample in order to compare the efficiency of each extraction. The error bars indicate the 95% confidence interval for each data set.

Referring to FIGS. 1 to 4, there are shown various views of a tissue sampler 2 according to the invention, which can be used to extract samples 14 from whole or disrupted bodies or body parts. The sampler 2 is simple to use and the sample material 14 gathered therewith can be used with a single extraction protocol, which can be applied either at the scene (ie "hot zone"), for example, using mobile lab-on-a chip technology, or in a laboratory elsewhere. The most common tissue harvested using the sampler 2 is muscle as this is easily identified in both whole and disrupted bodies. However, it should be appreciated that the sampler 2 could be used for sampling solid organ tissue, as well as fat. The sampling device 2 provides a unified system for the sampling of a small (mg amounts) sample 14 of muscle or organ tissue from whole or disrupted remains at the scene where they lie, ie the site of death, or elsewhere, eg at a temporary mortuary.

As shown in FIG. 1, the tissue sampler 2 consists of two main components, ie a container 6 and a sample collector 4.

The container 6 comprises a transparent plastic tube. The lower end of the container 6 is bonded to a base 7 that, when placed on a substrate, supports the container 6 in an upright orientation. The upper end of the container 6 is externally threaded for engagement with the closure assembly 4.

The sample collector 4 is also made principally of plastic and comprises an internally threaded cap 4a with a pair of ourtwardly extending limbs 5 by which the closure assembly can be grasped by a user and screwably engaged with the container 6. When so engaged, the closure assembly 4 seals the container 6. In alternative embodiments, the closure assembly may have an interference or snap fit with the container 6. Also, the sample collector 4 may includes a child-proof or tamper-proof device to inhibit opening of the device once a sample 14 is within the container 6. The sample collector 4 may also include a tearaway seal (not shown) to ensure that the device has not been tampered with prior to use. The colour of the closure assembly may also be used to indicate different preservative types, as discussed hereinafter. The sample collector 4 or the container 6 can include a tag such as a radio frequency identification device (RFID) 11 for labelling and tracking of the sample 14. The sealed sampler 2 with a sample 14 therein can be shipped to a remote location for analysis, by mail or other means.

An elongate hollow punch 8 depends from the underside of the cap 4a such that, when the sample collector 4 is engaged with the container 6, the punch is disposed coaxially with the container 6. The punch 8 is about 5 cm in length and is used to biopsy or extract a tissue sample 14 from a subject (eg a corpse or body part). The sample collector 4 and punch 8 can be formed integrally as a one piece moulding, or they may be separate components that are bonded together, eg using adhesive or welding. The sample collector 4 can be unscrewed from the container 6 with the punch 8 attached. Thus, the sample collector 4, and in particular the limbs 5, gives an operator a robust handle with which to grip the device 2 as it is used on the subject, thereby keeping the hand of the operator away from the punch 8 at all times, and minimising the risk of puncture, injury or contamination.

As shown in FIG. 2, the punch 8 is cylindrical in shape, having a diameter of about 4 mm, although the diameter of the punch 8 can vary depending on the type of sample 14 required, for example between 2 mm and 8 mm. In a first embodiment, the punch 8 is made of stainless steel. However, the punch 8 does not have to be made of stainless steel. The shaft can be made from any suitable material that is rigid and sufficiently sharp to cut through semi-solid or elastic surfaces to access samples within a subject. In another embodiment, the punch 8 may be of composite construction, with a rigid plastic shaft and a stainless steel cutting tip 16, as shown in FIG. 2.

The cutting tip 16 of the punch 8 is open-ended having an opening which is suitably sized to receive a sample 14 once it has been cut from the subject. The cutting tip 16 of the punch 8 is sharp, to cut into the body or subject. In the illustrated embodiments, two cutting wires 18 extend across the opening in the tip 16 of the punch 8, and are provided for cutting the sample 14 out of the subject, as described below. The wires 18 are fixed to the tip 16 of the punch 8 by welding.

FIGS. 3 and 4 illustrate two different embodiments of the arrangement of the cutting wires 18 with respect to the opening in the tip 16 of the punch 8. In the embodiment shown in FIG. 4, the wires 18 form a cross across the opening in the tip 16 of the punch 8. In the embodiment shown in FIG. 3, the cutting wires 18 extend across the opening of the tip 16 of the punch 8, but are spaced apart and parallel with each other. Both embodiments of cutting wire 18 have been found to be effective at cutting a tissue sample 14 out of the body. However, it is believed that the embodiment shown in FIG. 4, in which the wires 18 form a cross, is more effective.

As shown in FIG. 1, the container 6 contains a solution of preservative 12, which is provided to preserve the tissue sample 14 and the DNA therein after it has been biopsied from the body until such time that it is analysed. The solution 12 preferably has a long shelf life both before use and with the sample in it, and has two main functions. Firstly, it should preserve the sample in the container 6. The sample may therefore be stored at room temperature thus allowing the device 2 to be stored and used anywhere in the world in any environment, without the need for freezing or even refrigeration of the sample. Secondly, the solution 12 should start the DNA extraction process from the sample as soon as it is placed therein, thus speeding up the process and making it possible to undertake on-scene DNA analysis. This reduces the need to handle or dissect the sample in the laboratory, thereby avoiding risk of sample contamination.

In addition, the solution 12 can be used to decontaminate the sample thereby improving storage thereof. This can be achieved for biological contaminants by use of an anti-microbial agent as these do not interfere with the processes involved in DNA profiling. The solution 12 is compatible with present and foreseeable DNA profiling techniques using commercially available techniques or lab-on-a-chip technology.

Two embodiments of preservation solution 12 designed for room temperature preservation of field-collected samples were investigated. The first embodiment, referred to herein as Solution A, is commercially available and consists of Oragene DNA Self-Collection kit from DNA Genotek, Ottawa, Ontario, Canada. The second embodiment of preservation solution 12, referred to as Solution B (lysis storage and transportation buffer, LST), consists of 100 mM Tris-HCl (pH 8.3); 0.5M KCl; 4.5% Nonidet P40; 4.5% Tween 20; and 1% Sodium Azide, as disclosed in Muralidharan, K. and Wemmer, C. (1994) Transporting and storing field-collected specimens for DNA without refrigeration for subsequent DNA extraction and analysis (Biotechniques, 17, 420, 422). The solution 12 contains an anti-microbial agent, such as sodium azide, and could also have a component to decontaminate chemical contamination. The solution 12 has a long shelf life (at least 5 years) both for storage, and after use. The solution 12 is also able to be stored at room temperature, even with the DNA sample within, thus eliminating the requirement for refrigeration or freezing post collection.

As shown in FIGS. 1 and 2, the punch 8 includes a series of spaced apart openings 9, which extend through the side wall thereof. The openings 9 are spaced apart along the longitudinal axis of the needle 8, there being two series of such openings 9, at diametrically opposed sides of the punch 8. The openings 9 are provided in order to allow preservative solution 12 to pass from the container 6 to the inside of the punch 8 such that the solution contacts and soaks the sample. This improves the preservation of the sample inside the punch 8. This is useful if the sample 14 is to be stored in the sampler 2 for extended periods of time before being analysed. The openings 9 however should not be so large that the sample 14 can fall out of the punch 8.

In use, an operator first unscrews the sample collector 4 from the container 6 in which approximately 10 ml-20 ml of preservation solution 12 (eg solution A or B) is contained. The tip 16 of the punch 8 is placed onto the surface of a test subject at the point of biopsy, ie from where the tissue sample is to be extracted from the subject. Generally, the tissue sample is a small piece of soft tissue, such as muscle. The operator pushes down on to the sample collector 4, thereby urging the cutting tip 16 of the needle 8 into the subject such that the cutting wires 18 are urged into and cut into the subject. In so doing, a sample 14 is cut out of the subject, and is urged into the hollow lumen of the punch 8. The operator continues to push the sample collector 4 and hence punch 8 into the subject to ensure that a sample 14 of sufficient size (about 1 cm in length, and about 4 mm in diameter) has been cut out of the subject, at which point the punch 8 is then pulled away from the subject. This movement causes the cutting wires 18 to cut the sample 14 so that it is free to be pulled out of the subject for storage purposes. If desired, a slight rotation or twisting action may be applied to the sample collector 4 and hence punch 8 to improve cutting of the sample 14 and removal thereof from the subject.

The cutting wires 18 cut the first end of the sample as the punch 8 is pushed into the subject and also the second end of the sample as the punch 8 is pulled away from the subject. However, the cutting wires 18 not only serve the purpose of cutting into the subject and for separating the sample 14 therefrom. They also retain the sample 14 inside the hollow lumen of the punch 8, preventing it from falling out.

Once the sample 14 has been biopsied from the subject, the sample collector 4 including the punch 8 is placed back on to the container 6, and tightly sealed thereto such that the preservative solution 12 does not leak out. The sample retained in the distal end 16 of the punch 8 should now be fully immersed in the preservative solution 12 so that the DNA in the sample is preserved for subsequent analyses. It will be appreciated that it is imperative that the DNA in the sample is fully preserved to facilitate the DNA analysis conducted thereon, and to ultimately improve the speed and accuracy of the identification analyses.

The tissue sampler 2 includes a label 10 with a unique identification number, such as an Association of Chief Police Officers (ACPO) 6,000,000 number. The label 10 may also include a barcode label to improve identification and cataloguing. The label 10 may show the manufacture date and expiry date of the sampler 2.

The sampler 2 is sterilised and certified DNA free prior to use. This ensures that aDNA profile generated from the sample 14 is derived from the sample 14.

Further details of the experiments and methodologies used in the development of the present invention and its method of use are described in the following.

Methods

Models Used for DNA Sampling

Several models were used to test both the sampling and storage systems. Preliminary work involved collection of muscle samples from the upper right thigh of whole human cadavers using a variety of needle and needle biopsy sampling systems. Two samples were taken from each subject. One sample was placed into solution A, and the other into solution B. A swab of blood from the sample site was then taken from each subject as a control sample. This model was used to consider the sample retrieval system and the type of fluids used in the sampling system. Human lower limbs were donated to the Leicester University Forensic Pathology Unit for the purpose of identification research. These were subject to a number of experiments.

1) In order to investigate the rate of DNA degradation in fragmented body parts, donated limbs were left indoors and outdoors for a period of 2 weeks to naturally decompose. Each day a small sample was taken for immediate DNA extraction to assess the level of DNA degradation that had occurred due to decomposition. This experiment assessed the tissue sampling system used and the effect of decomposition on the ability to retrieve DNA profiles using the sampler 2.

2) In order to consider the rate of DNA degradation in smaller human fragments, twenty eight pieces of muscle were removed from donated human lower limbs and placed into medicine pill boxes. The muscle pieces were stored indoors at room temperature to decompose over a period of 28 days. Each day one piece was removed and processed to consider the effect of time on DNA extraction.

3) Samples were collected from the following organs of cadavers; brain, muscle, fat, heart, lung, liver, kidney, spleen, bone marrow and bowel. They were placed into solution A and B as well as one piece being frozen. A range of cadavers from fresh to decomposed were sampled. This model considered the use of all major body organs and soft tissue with the sampling system and the effect of decomposition on the ability to extract DNA from different body sites.

4) Pieces of muscle were removed on receipt of two limbs and placed into the solutions to assess the amount required to be sampled in the sampling system. Samples weighing 1000, 500, 250, 100, 50, 25, 10 & 5 mg were placed into solution A. Samples weighing 1000, 500, 250, 100 & 50 mg were placed into 5 mls solution B and finally, samples weighing 100, 50, 25, 10 & 5 mg were placed into 1 ml solution B. DNA extraction was performed on each sample at 1 week, 2 weeks, 1 month, and 3 months time points to assess DNA quality. Further work to consider 6 months, 1 year and 2 year time points continues within the Unit.

DNA Extraction Kits

During the development of the sampler 2, the inventors considered how the DNA would be extracted from the sample to ensure that any solution used is compatible with the extraction system. An internet based search was undertaken to identify commercially available DNA extraction kits to identify the best approach to DNA extraction from both solid tissue and tissue stored in preservation buffer. This search revealed nine commercially produced kits, any of which may be employed in the present invention:—

1. Phase lock gel, Eppendorf, Hamburg, Germany: a separation medium for use with phenol-chloroform DNA extraction procedures, designed to 'lock away' the protein component of the sample during extraction. This system was considered for CBRN DNA work as any harmful protein components of bacterial or viral contaminants that could not be made safe by digestion would be trapped in the protein phase of the gel for safe disposal. However, a potential drawback with this system was that phenol has to be used, and the technically demanding nature of this type of extraction.
2. Charge Switch technology—forensic kit, Invitrogen, Carlsbad, Calif., USA: These kits are based on magnetic bead separation, whereby DNA is bound to beads under high salt conditions and held by magnetic force to allow the removal of protein and other contaminants before elution of pure DNA under low salt conditions. There are many different kits now available for specific applications such as buccal swabs and blood. They are also suitable for automation using robotic workstations.
3. GENELUTE, Sigma, St Louis, Mo., USA: Designed for use with blood.
4. PicoPure DNA Extraction kit, InVisorb, InVitek, Berlin, Germany: Several kits available for use with small (<100 cells) tissue samples, blood, stool etc.
5. DNA IQ & Wizard kits, Promega, Madison, Wis., USA.
6. MAGNA PURE, Roche, Basel, Switzerland: Automated DNA extraction instrument. Reagents available for different starting materials.
7. Dr GenTLE, Cambrex, Charles City, Iowa, USA: Kit designed for DNA extraction from blood only.
8. Oragene DNA self collection kit, DNA Genotek, Ontario, Canada: This kit has recently been developed for the collection of saliva samples for extraction of high quality DNA. This is a room temperature storage and preservation system, and is one of the preferred systems employed in the sampler 2 according to the invention.
9. Qiagen DNA Mini & Micro kits, Qiagen, West Sussex, UK: These kits are frequently used by the inventors and have been found to be both reliable and versatile for use with different starting materials. These kits are also designed for use with robotic extraction platforms such as the Qiagen Biorobot. Robotic DNA extraction not only increases the throughput of DNA extraction but will also remove the risk of operator contamination when processing CBRN contaminated materials.

EXPERIMENT 1

Pilot Study

Preliminary work to quickly assess the solution's ability to preserve DNA integrity at room temperature were carried out on small muscle samples collected from six cadavers at Leicester Royal Infirmary by Professor G. N Rutty. Sampling was carried out on a range of cadavers with varying post mortem history, from newly deceased to badly burnt. Conventionally, a number of samples can be taken from the body for the purpose of DNA identification. Muscle is a recognised sample type. Usually large quantities of muscle are recovered from the body, typically of the order of 0.5 g to 5 g or more. This is normally done using a scalpel and forceps. However, this size of sample may not be necessary. The inventors have found that sample sizes of less than 100 mg are perfectly adequate. This may however depend upon early sampling of the body to avoid the effect of severe decomposition. DNA extracted from muscle stored at room temperature in solutions A & B was compared to DNA extracted from control blood swabs and muscle stored frozen at −20° C.

A full ten 10 loci short tandem repeat (STR) profile was easily obtained from all samples, with no evidence of accelerated DNA degradation in any sample stored at room temperature for up to 19 days before processing. Referring to FIG. 5, there is shown an example of a full second generation multiplex (SGM) plus profile.

EXPERIMENT 2

The Limb Model

It is known that the most influential factor affecting successful DNA profiling for Disaster Victim Identification (DVI) is the time between incident, sample collection and preservation. This experiment was undertaken to assess the time frame for successful DNA sampling after a CBRN incident. This experiment has assessed the DNA degradation patterns of amputated human limbs donated to the Forensic Pathology Unit by patients of the University Hospitals of Leicester, NHS Trust. It is designed to simulate body fragmentation following an explosive CBRN incident that may occur indoors or outdoors.

A total of seven amputated limbs were investigated during this example. Two were dissected into small 2 cm×2 cm×1 cm cubes to asses DNA degradation in fragmented muscle pieces. Five (2 indoors and 3 outdoors) were used as whole limb models. Two different laboratory set ups were utilised with the limb and tissue sample models. These were used to consider indoor and outdoor environments with whole and fragmented limb models.

The indoor environment used a secure, private, dedicated extraction fume cupboard within the Forensic Pathology Unit. The limb and tissue samples within the pill boxes were placed into the cabinet. The temperature was continuously monitored and there was a steady extraction airflow through the cabinet. Commercial deodoriser solution designed to be used with products of decomposition was placed into the cabinet to minimise the odour of decomposition. No fly infestation occurred in this model. The samples were checked, sampled and photographed each day, seven days a week.

The outdoor model used whole limbs only. These were placed into rabbit hutches on top of a University of Leicester building. The environmental temperature and humidity as well as fly infestation were continuously monitored. The samples were checked, sampled and photographed, 5 days a week only, due to limited roof access.

As stated previously, it was believed that only relatively small samples would be required for use with the concept system. To test this, a small sample (approximately 20 mg) of muscle tissue was collected each day at approximately 12:00 for DNA extraction using the Qiagen DNA Mini kit—Tissue protocol (Qiagen, West Sussex, UK). The weight of muscle tissue used in each extraction was recorded to allow for direct comparison between samples taken on different days, and from different limbs. The temperature of the fume hood was recorded twice (AM & PM) everyday and a temperature and humidity data logger was placed on the roof with the outdoor limbs to record temperature.

DNA quantity was measured by spectrophotometry using the Nanodrop-1000 system, (Nanodrop Technologies Wilmington, Del., USA). DNA quality was assessed by 1% (w/v) agarose gel electrophoresis in 1×TAE buffer, gels were run at 100V for 2 hours. A 1 kb ladder was run on each gel and degree of DNA degradation was assessed by mobility of most degraded fragments and scored on a scale of 10 to 0 based on fragment size, with 10 being un-degraded high quality DNA and 0 being severely degraded poor quality DNA. An example of the scoring system is shown in FIG. 6.

Rather than degrading, the DNA quality within the small fragmented muscle pieces remained the same (grade 10)

throughout the two week sampling period. This is due to rapid desiccation of the muscle pieces in the fume hood leading to preservation of the DNA within the dried tissue. Although it is unknown whether this rapid desiccation would occur in other environments such as in an underground tube station or outdoors in a stadium, this result indicates that even small (<5 cm$^3$) tissue samples are suitable for DNA identification after a CBRN incident. This observation is in keeping with previous experience of DNA identification undertaken from fragmented body parts retrieved after a mass fatality road traffic accident in 2006.

The results show that DNA degradation begins 3-4 days following limb avulsion independently of location (indoors/outdoors) and accelerates rapidly after initiation. Infestation does not appear to accelerate this process. Current DNA profiling technology can allow for full DNA profile production from tiny amounts of heavily degraded DNA, the processing of such difficult samples is, however, much more technically demanding and time consuming and is not easily automated.

Most commercially available DNA profiling kits are optimised to utilise 1-2 ng DNA for profile production. DNA quantities far in excess were obtained from all samples indicating that only minute samples are required for successful DNA profile production for DVI. Following a CBRN incident, especially if the specific agent or associated risk is unknown, the collection of minimum quantities of biological material for DNA analysis will reduce the risk of transportation and processing of contaminated materials.

EXPERIMENT 3

Identification of Materials that can be Collected

Rough guidelines for collection of approximately 100 mg each tissue was given to the pathologists responsible for sample collection. Collection was requested to be carried out on cadavers of varying post mortem history to assess the ability of the solutions to preserve decomposed as well as fresh material. Samples of muscle, brain, heart, lung, liver, spleen, kidney, bowel, fat and bone marrow were requested to represent a range of tissue types and locations throughout the human body. It is known that in whole, undisrupted cadavers that organ decomposition is usually observed to follow a predictable pattern, starting in the intestines and stomach followed by the airways and lungs, then kidney and bladder, brain and CNS, then skeletal muscle and finally the connective tissues. It is not known if DNA degradation follows the same pattern of degradation.

Three samples, of approximately equal size/mass were collected for each tissue type. One was placed into an 8 ml plastic screw top container for storage at −20° C., the other two pieces were stored at room temperature, one in Oragene solution and one in 5 ml Lysis Storage and Transportation (LST) buffer. This would allow for a direct comparison between classical (freezing) and experimental storage methods.

Previous examples have concentrated on the ability of the chosen solutions to preserve DNA in muscle tissue. The following work investigates the ability of the same solutions to preserve other human tissues that may be recovered for identification purposes after a CBRN incident, especially one of an explosive nature where the resulting fatalities would be disrupted. This example also demonstrates the storage and transportation of various tissues that may be recovered after a mass fatality incident, with sample collection and room temperature storage being undertaken in Germany, before undergoing refrigerated transport via courier to the Forensic Pathology Unit, Leicester, UK for processing.

Referring to FIGS. 7 and 8, there are shown bar charts summarizing the concentration of DNA that may be obtained for various tissue types when using LST buffer and Oragene buffer, respectively. The DNA quality was again assessed by 1% agarose gel electrophoresis in 1×TAE.

FIG. 9 depicts three 1% agarose gel images to assess the quality of DNA preserved by freezing at −20° C. (left), LST buffer (middle) and Oragene buffer (right). A DNA ladder is included in the first lane of each gel image. All following lanes contain DNA extracted from tissues in the following order: Muscle, brain, heart, lung, liver, spleen, kidney, bowel, fat & bone marrow from left to right. The bands present in this ladder correspond to the fragment size of DNA in the gel, ranging from 1000 base pairs up to 10,000 base pairs. DNA degradation is assessed by the length of DNA fragments present in the visualised sample, DNA above 10,000 base pairs in length is considered as high quality, anything below this size is considered as degraded. The extent to which DNA is degraded is assessed by the remaining fragment sizes, the smaller the DNA (or how far down the gel the DNA can be observed) indicates how degraded a sample is. The results shown in FIG. 9 indicate that the sampled DNA containing material can be preserved equally by freezing, LST and Oragene buffers, demonstrating that room temperature storage is appropriate for preservation of samples recovered from partially decomposed subjects.

The results of this section demonstrate that high quantities of DNA can be rapidly extracted from a multitude of tissue types using standard DNA extraction protocols designed for use with muscle tissue. The amount of DNA recovered is dependent on tissue type rather than storage method, as can clearly be observed in the Figures. The knowledge that any tissue type can be collected after a CBRN incident for DNA profiling will again reduce the amount of time that must be spent examining the body or body part for suitable tissue.

As shown in FIGS. 7 and 8, although an amount of DNA in excess of that required for DNA profiling was recovered from all tissue types, the quality of the DNA does differ between different tissue types as shown in FIG. 9. DNA extracted from muscle, brain and heart showed the least degradation. The extent of degradation between all other tissue types appears to be equal. A comparison between the DNA quality of tissue taken from the same body but stored by different methods also reveals that both Oragene buffer and LST buffer are equally or more effective at preserving the quality of DNA for short periods of time (up to 64 days) at room temperature than the traditional method of freezing.

An additional benefit of using room temperature storage buffers is that DNA extraction can be performed directly on aliquots of the solution, ie no additional processing of tissue is required. With samples stored at −20° C., before extraction can be undertaken the sample must first be defrosted, removed from its container, dissected, weighed, macerated and then digested for 1-3 hours (or overnight in many cases). This processing not only requires a great deal of time but will also place the DNA analyst at risk following a CBRN incident by requiring that samples must be handled and cut before extraction. The use of a preservation solution removes this risk entirely as DNA can be extracted from small aliquots of untreated buffer, using shorter DNA extraction protocols. The ability to extract directly from aliquots of the storage buffer will also allow for the automation of the entire extraction process by use of robotic platforms such as the Qiagen Biorobot, removing any risk posed by CBRN contaminated samples, and increasing the throughput of the entire processing.

EXPERIMENT 4

Determination of—Quantity of Sample Required and Long Term DNA Preservation at Room Temperature In order to determine how much material must be placed into each solution for optimal DNA preservation and extraction, muscle tissue excised from two donated human limbs was dissected and carefully weighed out in increments of 5-1000 mg to be placed into solution A and solution B for room temperature storage. The volume of LST buffer required was also investigated with muscle pieces being preserved in either 1 ml or 5 ml.

To assess the solutions' ability to preserve DNA at room temperature, extractions were performed using 100 µl aliquots of each solution using the Qiagen DNA mini kit—blood/body fluid protocol, after 1 week, 2 weeks, 4 weeks and 12 weeks. The quantity of DNA recovered was recorded as ng per µl solution. DNA quality could not be assessed by agarose gel electrophoresis as the quantity required for visualisation by this crude method was not recovered when smaller (<500 mg) tissue pieces were placed into preservation solution.

Referring to FIG. 10, there is shown DNA from muscle in solution A and muscle in solution B sampled over a 12 week period.

Key for figures a-d:

| Lane | Sample |
|---|---|
| | Muscle A |
| 1 | 1 kb ladder |
| 2 | 100 mg in 1 ml LST buffer |
| 3 | 50 mg in 1 ml LST buffer |
| 4 | 1000 mg in 5 ml LST buffer |
| 5 | 500 mg in 5 ml LST buffer |
| 6 | 1000 mg in Oragene buffer |
| 7 | 500 mg in Oragene buffer |
| | Muscle B |
| 8 | 1 kb ladder |
| 9 | 100 mg in 1 ml LST buffer |
| 10 | 50 mg in 1 ml LST buffer |
| 11 | 1000 mg in 5 ml LST buffer |
| 12 | 500 mg in 5 ml LST buffer |
| 13 | 1000 mg in Oragene buffer |
| 14 | 500 mg in Oragene buffer |

This study was designed to investigate several variables simultaneously. The decision to examine multiple factors was taken due to the short time frame and unpredictable availability of sample material. The results presented give information on how much muscle is required, what volume of buffer is required for sample/DNA preservation and the effect of time on DNA stability in Oragene buffer. The results of DNA extraction and DNA profiling performed during this project indicate that both solution A and solution B are capable of preserving DNA at room temperature for up to three months. Based on testing carried out within the inventors' labs, it is however anticipated that DNA will be preserved for over 1 year at room temperature and for longer time periods in solution A or B at −20° C.

The results of DNA quantification indicate that as little as 5 mg muscle tissue is sufficient for recovery of enough DNA for standard profiling to be undertaken. A direct relationship between weight of muscle tissue and DNA quantity extracted from 100 µl buffer is also demonstrated. Although vague, current guidelines for collection of biological material for DVI recommend that large (1-10 g) portions of tissue should be retained to ensure adequate material is available for DNA profiling. The collection of smaller (5-10 mg) biological samples following a CBRN incident will reduce the amount of contaminated material that is required to be transported from the 'hot-zone' to a laboratory, fixed, temporary or mobile, for further processing.

The optimal amount of collected tissue has not been determined from the results of the above experiment although the work undertaken to date indicates that as little as only 10-200 mg of any tissue is required for identification purposes. The inventors were particularly surprised at this result. The amount of tissue collected does influence the DNA quantity that is recovered after processing. The effect of tissue quantity on DNA quality has not however been accurately determined. SGM Plus DNA profiling on DNA extracted from both 5 mg and 1000 mg samples in both Oragene and LST buffers gives similar results, namely full profile generation with evidence of slight DNA degradation. The efficiency of DNA extraction increases as the amount of tissue preserved decreases. This may be due to a relationship between surface area and volume ratio of the muscle pieces whereby smaller tissue samples will become more completely digested, releasing more DNA into the surrounding solution, which is then collected for DNA extraction.

This quality of the buffer solutions, to equally preserve tissue weighing between 5 and 1000 mg is advantageous in the collection of material after a CBRN incident as it does not appear critical that a specific amount of tissue is collected. Less time can therefore be spent in the 'hot-zone', minimising the risk to the collection operator.

It should also be noted that approximately twice the amount of DNA is recovered from Oragene buffer compared to LST buffer when equal amounts of muscle tissue have been preserved. This may be due to an extra incubation step (overnight at 50° C.) that is included in the extraction of DNA from Oragene. This incubation stage is recommended by the manufacturer of the Oragene solution but was omitted from the LST buffer extraction. A simple experiment to compare the quantity of DNA recovered from 50 mg muscle tissue in 1 ml LST buffer after incubation at room temperature, 56° C. and 70° C. was subsequently carried out, and the results are shown in FIG. 11.

Although this experiment was carried out in triplicate, with the average values and standard deviation of results being shown in FIG. 11, no statistically significant conclusion can be made on such a small data set. However, it does appear that increased amounts of DNA are recovered after DNA extraction when an incubation stage at 56° C. and 70° C. is included in the protocol.

EXPERIMENT 5

Buffer Solutions

Two buffer solutions were investigated for their ability to preserve soft tissue samples at room temperature preservation over a 52 week time period.
Materials and Methods
Sample Collection Two lower limbs were collected from adult amputation patients. Both limbs were amputated due to chronic lower leg ischemia caused by diabetes. Immediately after amputation the limbs were taken to the Forensic Pathology Unit, and viable muscle tissue was dissected from the limb. Muscle was chosen as it is a dominant soft tissue type throughout the body and is often present and easily identifiable in fragmented body parts.

Preservation Methods

Two methods of room temperature storage were identified by literature review: lysis storage and transportation (LST) buffer consisting of 100 mM Tris-HCL pH 7.6, 0.5M KCl, 4.5% Nonidet P40, 4.5% Tween 20 and 1% sodium azide [4,5] and the Oragene™ DNA self-collection kit (DNA Genotek, Ottawa, ON, Canada).

Experimental Design

Pieces of muscle were removed on receipt of each of two limbs and placed into the solutions to assess the amount required to be sampled in each buffer and for how long DNA is preserved at room temperature. Samples weighing 1000, 500, 250, 100, 50, 25, 10 and 5 mg were placed into Oragene™ collection pots. Samples weighing 1000, 500, 250, 100 and 50 mg were placed into 5 ml LST buffer and finally, samples weighing 100, 50, 25, 10 and 5 mg were placed into 1 ml LST buffer. DNA extraction was performed on each sample after 1, 2, 4, 12, 36 and 52 weeks.

DNA Extraction

Samples Preserved at Room Temperature

Incubation at 50° C. for 3 h was performed for all Oragene™ preserved samples—as per manufacturers' instructions. The Oragene™ purification protocol involves the addition of $\frac{1}{25}^{th}$ Oragene™ purifier solution to the sample and incubation on ice for 10 minutes. This is then followed by a series of centrifugation and wash steps to finally recover the DNA in pellet form which requires re-hydration in a chosen volume of buffer or water. This purification technique, recommended by the manufacturer was designed for use with saliva samples and was found to be insufficient for purification of DNA from muscle samples, as undigested tissue was present in the sample after repetition of the purification step three times. The recommended protocol was abandoned in favour of the Qiagen DNA mini kit (Qiagen, West Sussex, UK) which is designed to recover DNA from a number of different body fluids and tissues by inclusion of additional digestion stages depending on which protocol is chosen: 100 µl aliquots were removed from both Oragene™ and LST preservation buffers for DNA extraction using the Qiagen DNA mini kit—blood/body fluids protocol as per manufacturers' instructions. DNA was eluted in 100 µl buffer AE (Qiagen).

DNA Quantification

DNA quantification was carried out on 1 µl of each extracted sample in duplicate using the Quantifier Human DNA Quantification kit (Applied Biosystems) in a total reaction volume of 12.5 µl. Thermal cycling was carried out on a 7500 Real-Time PCR System (Applied Biosystems) according to manufacturers' instructions.

DNA Profiling

Profiling was carried out on DNA from all extracted samples using the AmpF/STR® SGM Plus® PCR Amplification kit (Applied Biosystems, Foster City, Calif.) in a final reaction volume of 12.5 µl. 1 ng template DNA was added to each reaction whenever possible. Initial DNA profiling was carried out using 28 amplification samples. Samples for which a partial or failed DNA profile was observed after 28 cycles were re-amplified for 34 PCR cycles. PCR products of week 1, 2, 4, 12 and 36 extracts were separated and visualised on an ABI PRISM® 377 DNA Sequencer (Applied Biosystems). Fragment sizing was carried out using GeneScan® software version 2.1 (Applied Biosystems) and allele designation was carried out using Genotyper® software version 3.7 (Applied Biosystems). PCR products of week 52 extracts were separated and visualised on an Applied Biosystems 3130 Genetic Analyser and were analysed using GeneMapper ID software version 3.2 (Applied Biosystems).

Results

DNA extraction was carried out on 100 µl aliquots of each preservation buffer. The results of DNA quantification of samples stored at room temperature in both Oragene collection pots and LST buffer are given in the table shown in FIG. 12. The average temperature of the room in which samples were stored was 24.2° C. with a minimum temperature of 16° C. and maximum temperature of 30.5° C. during the 52 week period. The quantity of DNA recovered after each extraction remains consistent for extractions performed up to 12 weeks after this study was initiated. The quantity of DNA recovered shows an increase in yield at week 36 and 52. These results may be explained by the decreased volume in which samples were stored as repeated sampling from the same container resulted in the total buffer volume being reduced by 100 µl following sampling at each time point. The Ct values for all quantified samples were in the expected range (20-35) indicating that no PCR inhibition occurred during template amplification. The results of DNA quantification were analysed using an ANOVA. There was no significant difference in the yield of DNA for either muscle A (p>0.2) or muscle B (p>0.5) for any sampling time point. The DNA yield from solutions containing muscle A and B was analysed using a paired t-test, assuming no variance. There was no significant difference observed for the total quantity of DNA recovered from muscle A or B.

As there was no significant difference in the yield of DNA obtained between samples extracted from muscle A or B, or between the time point at which sampling was carried out, the results were complied to assess the efficiency of DNA extraction for each mass of tissue stored in each preservative solution.

FIG. 13 shows the average yield of DNA obtained after extraction was performed on 100 µl aliquots of preservative buffer for each mass of tissue stored in Oragene solution. This data has been normalised by dividing the total DNA yield by the amount of tissue in mg to allow each tissue mass to be directly compared and presented on a single chart. Similarly, FIG. 14 shows an evaluation of the DNA recovery efficiency for muscle tissue stored in 5 ml LST buffer and FIG. 15 for tissue stored in 1 ml LST buffer. The results presented in FIG. 1 suggest that storing 500 mg tissue in Oragene collection pots results in an optimal DNA recovery ratio and FIG. 15 suggests that the greatest DNA recovery efficiency for samples stored in 1 ml LST buffer is achieved when 5 mg tissue is stored. The results presented in FIG. 15 suggest that 100 mg tissue should be stored in 5 ml LST buffer to provide a maximum DNA return per mg tissue stored. The total yield of DNA recovered by extraction of 100 µl aliquots taken from containers holding 5 ml LST buffer and tissue samples however show a significantly reduced total yield compared to samples stored in Oragene pots and 1 ml LST buffer.

DNA profiling was carried out on 1 ng of template, or reduced amounts when DNA concentration was below 0.2 ng/µl, as 5 µl template was used for each reaction in a total volume of 12.5 µl. A full DNA profile was obtained for the vast majority of samples. A partial DNA profile, where allele and or locus dropout was apparent was observed in 8.8% of amplifications and amplification failure was observed in 2.8% of all samples, as indicated by asterisks in FIG. 12. All samples showing drop-out or failure were re-amplified using 34 PCR cycles. This resulted in full profile generation for all samples with a single exception. No DNA profile could be produced when attempting to amplify material recovered from the 100 µl aliquot taken from muscle A stored in Oragene preservative for 1 week. Additionally, this was the only sample to be undetected during DNA quantification. It is hypothesised that this is due to the very small tissue fragment adhering to the lid portion of the Oragene collection pot, preventing it from being in contact with the preservative solution during the first week of storage. Care was taken after this occurrence to ensure that tissue samples were present in the preservative solution, not adhering to the lid portion of Oragene collection points for all samples.

Of the samples that showed partial profiles following the first amplification, drop-out can be explained by the addition of inadequate template for the majority of samples, these profiles showed electropherograms typical of this cause, with low average peak height observed across all amplified loci. This observation was supported by the quantification data, with low (<0.04 ng/µL) quantities being recorded for these samples. Of the exception to this explanation, it is not known why a full DNA profile could not be produced when DNA extracted for 10 mg muscle tissue B was stored in Oragene buffer for 1 week as DNA quantification indicated that a concentration of 0.07 ng/µl DNA was recovered. The results of 34 cycle amplification produced a profile typical of addition of too much DNA template, with pull-up peaks observed due to peak heights exceeding 6000 RFU's in the electropherogram. This may be explained by a human error made during the first amplification attempt using 28 PCR cycles.

Partial profiles were also generated for tissue samples stored for 36 and 52 weeks when DNA quantification indicated that sufficient template was entered into each reaction for full profile generation after 28 PCR cycles. Although a full profile was generated after re-amplification using 34 PCR cycles, the electropherogram image demonstrated a pattern of amplification typical of degraded template, with lower peak heights observed for the longer loci in the SGM Plus amplification kit, such as D18552 and FGA. These results suggest that the quality of DNA recovered from muscle tissue stored in both Oragene and LST preservative buffers may begin to diminish after 6 months at room temperature.

A number of samples can be taken from the body for the purpose of DNA identification. In the majority of forensic cases whole, non-disrupted cadavers will be examined at autopsy. In such cases buccal swabs, liquid blood samples or blood spots on filter paper can collected for DNA profiling (depending upon where one practises in the world) due to the ease of laboratory processing of these sample types. In the United Kingdom (UK), even with whole bodies, psoas muscle samples may also be collected.

In situations where buccal cells and/or blood are not available, such as during the examination of highly fragmented remains, an alternative biological sample must be collected. In the UK recent incidents involving severe body disruption have lead to the decision for scene recovery of those body parts greater than 5 cm$^3$. Identification and re-association use this same tissue size. Thus in the case of fragmented bodies the predominantly available tissue type will be soft tissue rather than bone or teeth and as muscle is often present to these sample this investigation has focused on muscle tissue as an alternative source of DNA. It is widely acknowledged that DNA preservation in bone and teeth is superior to soft tissues, especially when putrefaction has occurred and in such circumstances bone or teeth samples will be as they may contain the only surviving DNA molecules. The processing of hard tissue is however extremely time-consuming and labour-intensive, requiring de-fleshing, cleaning, drying, cutting, grinding and de-calcification before DNA extraction can be carried out. Comparatively, the downstream processing of soft tissues will require a simple cutting and maceration step before DNA extraction is performed.

Similarly, under routine circumstances, sample collection for DNA profiling will take place during the autopsy examination, within a permanent mortuary facility. Samples can then be refrigerated or frozen to preserve the DNA. By cooling the samples many of the factors that contribute to DNA degradation, such as the action of endogenous enzymes and microbial/bacterial decomposition are slowed, or even halted at very low temperatures (−70 to −80° C.). In certain situations, including mass fatality incidents, depending on the location and number of victims, immediate refrigeration of samples may not be possible. Alternative methods of DNA preservation have been suggested for use in such cases. A low cost lysis storage and transportation (LST) buffer was developed for transportation and storage of field collected specimens, without refrigeration. This buffer contains a combination of chemicals designed to lyse cells, inactivate nucleases, prevent microbial growth and preserve the DNA. Original tests found LST buffer was effective for preservation of DNA for up to 8 weeks at room temperature from both blood and tissue samples. A subsequent publication, using clinical biopsy samples, directly compared the preservation capacity of LST buffer to snap-freezing and storage at −75° C. The findings of this investigation concluded that snap-freezing and storage at −75° C. was more effective at DNA preservation but also concluded that LST buffer is a suitable, cost-effective alternative for short term (up to 4 weeks) storage of tissue samples. The inventors feel that there is a role for such preservative solutions within this field.

The ability of both Oragene™ solution and LST buffer to preserve DNA present in fresh muscle tissue over a 12 month time period at room temperature has been examined. Results of these tests have shown that it is possible for full DNA profiles to be produced by use of standard DNA extraction and amplification procedures over this time period. Consideration of the quantification data suggests that the preservative solution contained within the Oragene collection pots is superior to LST buffer in recovery of high DNA yield, especially when compared to DNA yield of muscle tissue stored in 5 ml LST buffer, from which very low comparative yields were obtained. The results of DNA profiling carried out on all extracted samples does, however, suggest that the quality of DNA recovered from tissue stored in LST buffer is not significantly reduced compared to that recovered from samples stored in Oragene collection pots. The yield of DNA per mg of tissue stored was vastly greater when samples were stored in 1 ml rather than to 5 ml LST buffer, as illustrated in FIGS. 14 and 15. These results may suggest that LST buffer is better suited to the preservation of small (<100 mg) amounts of tissue. Due to the limited data set presented in this initial article, further investigation of this issue should be carried out before a conclusion can be drawn on the optimal volume of LST buffer required for sample preservation.

This experiment was designed to replicate the situation whereby multiple samples may need to be recovered from a single sample collected for personal identification of an individual who has lost their life during a mass fatality incident, for this reason multiple samples were not set up to provide a previously un-sampled specimen for each time point. The total volume of preservative solution of both LST buffer and Oragene was designed to be in excess of the volume required for sampling over a 1 year sampling period, totaling 600 µl. This resulted in a gradual reduction in the total volume of preservative solution held within each container during the 52 weeks for which sampling was undertaken. The increase in DNA yield after 36 and 52 weeks of tissue storage is most likely attributable to a reduction in the remaining tissue to preservative solution ratio due to the removal of 100 µl at each time point. The results of DNA profiling over the full 52 week sampling period do however suggest that multiple sampling from a single collected sample do not adversely affect the outcome to an extent that DNA quantity or quality slips below a standard required for use with current downstream processing and that individualisation of samples by DNA profiling can still be achieved.

Finally an additional benefit of using room temperature storage buffers is that DNA extraction can be performed directly on aliquots of the solution, i.e. no additional processing of tissue is required. With samples stored at −20° C., before extraction can be undertaken the sample must first be defrosted, removed from the container, dissected, weighed, macerated and then digested for 1-3 hours (or overnight in many cases). The use of a preservation solution removes this process entirely as DNA can be extracted from small aliquots of untreated buffer, using shorter DNA extraction protocols. The ability to extract directly from aliquots of the storage buffer will also allow for the automation of the entire extraction process by use of robotic platforms such as the Qiagen Biorobot (Qiagen, West Sussex, UK). This would allow for an increase in sample throughput and could allow for more rapid DNA profiling to be achieved than is possible with current protocols.

Recommendations

It has been demonstrated that both Oragene™ and LST buffers are suitable for preservation of muscle tissue for up to 12 months at room temperature, and as such could be used as an alternative to freezing of samples when refrigeration is not immediately available or where transportation of samples from one country to another may be required. The use of preservation solutions will also benefit the downstream processing of biological samples by removing the requirement for further manipulation of solid tissue. The fact that DNA extraction can be performed on an aliquot of either buffer solution, without further processing could also allow for automation of DNA extraction for high throughput processing of numerous soft tissue samples, if required. Another observation is that less material need be collected from corpses than current guidelines suggest. The findings show that a full SGM Plus STR profile can be obtained from as little as 5 mg muscle tissue, preserved in both Oragene™ and LST buffers for up to 52 weeks. In practice an amount of tissue weighing between 25 and 500 mg should ideally be collected for identification purposes to ensure adequate DNA quantities are available for multiple examinations. This system thus allows for the collection of small pieces of muscle (or other soft tissue) for room temperature preservation of DNA identification samples with potentially increased throughput by automated systems. It is fully portable and is compatible with bar-coding management systems. The initial results of ongoing work show that it is applicable to burnt remains and those showing changes of decomposition, both situations that may be faced during a mass fatality investigation and will be addressed in a subsequent communication. This builds upon previously published work using similar preservation buffers which have been promoted for DVI field work and is especially applicable in an incident involving disrupted body parts where traditional DNA samples or teeth and bone may not be readily available for identification and fragment re-association. This system should therefore be considered as an additional method for sample storage during DVI work.

Recommendations for CBRN

The following observations and recommendations are made following the work undertaken to date with regards to DNA identification following a CBRN incident. DNA can be used for cadaver identification following a CBRN incident. This will be dependent upon the type of contaminant involved in the incident. The inventors understand that a risk assessment would be undertaken of whether or not the body could be approached, that samples could be obtained and that these could be removed from the scene of incident prior to removing any sample from the body or the "hot zone". This would probably be undertaken by a Health Protection Agency.

It is unknown to date whether the size or nature of the sample that is proposed to be used in DNA identification would be either contaminated or pose a significant risk to the laboratory where the analysis would be undertaken. The analysis of the samples could be undertaken at the incident site, either within or outside the "hot zone" using either a temporary laboratory or mobile laboratory or at a commercial or private laboratory facility at a site remote to the incident. This would depend on the availability of a mobile laboratory or the provision of a temporary laboratory along the lines of the national mortuary equipment pods. Whether the samples, if taken, could leave the "hot zone" would depend upon the risk assessment undertaken in relation to the incident.

The inventors recommend the adoption of a uniform sampling and preservation system for not only a CBRN incident but all mass fatality or single cadaver DNA identification work. The inventors have identified preservation solutions A and B that can be used to preserve small samples of muscle or solid organ in non-refrigerated conditions for at least 3 months. By using such an approach, one uses a standardised approach to tissue sampling, standard preservative solution, and standardised protocol for extraction and analysis using commercially available kits and equipment that are compatible with present and predicted DNA identification systems.

Although the specific risks associated with processing CBRN contaminated materials is currently unknown, it is recommended that if DNA identification is to be undertaken that samples should be collected as soon as possible and not more than 3 days after the incident to ensure optimum DNA quality and minimise processing of contaminated samples to reduce operator exposure by allowing for rapid, or automated processing of collected materials. The body or body parts do not have to be recovered, just sampled.

The results presented herein also demonstrate that DNA extraction can be performed on a wide variety of tissue types, found throughout the human body including bowel and fat. It is therefore recommended that any soft tissue, deemed accessible can be collected for DNA extraction. It has also been shown, through investigation of muscle pieces, amputated limbs and whole bodies, that DNA can be recovered from human remains found in any state of completion or fragmentation. The use of commercially available diagnostic biopsy systems have been found to be unsuitable for collection of soft tissue from whole and fragmented bodies. It is therefore recommended that biological samples continue to be collected using a scalpel and forceps. This can be done within a CBRN environment wearing CR1 PPE without risk of injury as long as the person undertaking the sampling is competent in the procedure. To date this would normally be undertaken by a pathologist although anyone with suitable training could undertake the procedure. These samples can be placed in to the preservative solution, which can be within a container pre-labeled with the ACPO 6,000,000 number. A bar code system can be utilised.

It has been demonstrated that as little as 5 mg and as much as 1000 mg soft tissue is sufficient for accurate DNA profiling using a commercially available STR amplification kit. Some allelic drop-out was observed after DNA profiling from 5 mg tissue, a full profile was however obtained after re-amplification using a larger portion of the extracted DNA. It is therefore recommended that between 10-200 mg soft tissue is collected for DNA identification in the event of a CBRN incident. This amount will ensure sufficient DNA is collected and minimal risk of contamination is maintained by transportation of small quantities only.

Two preservation solutions were examined for their ability to preserve DNA at room temperature, to remove the requirement for emergency refrigeration facilities at incident scenes. Both solutions have been shown to preserve DNA from muscle tissue for up to 3 months, with no refrigeration or freezing. Work continues in relation to other body tissues although work undertaken to date supports that this statement is applicable to any soft tissue. The digestive action of both solutions also removes the requirement for DNA analysts to handle collected tissue, greatly reducing risk of operator contamination from infected samples. It is therefore recommended that in the event of any MFI or CBRN incident that biological samples collected for DNA identification purposes be placed into either solution A or B for preservation.

The invention claimed is:

1. A portable sampling device for obtaining and preserving a biological sample from a subject, the device comprising a sample collector for excising a biological sample from a subject, a sample container for containing excised sample, the sample collector being adapted, in use, to cut into the subject and release the biological sample therefrom and comprising a punch with an opening in its tip which leads to a channel which extends at least partially through the punch such that, in use, the biological sample is held within said channel;

wherein the sample collector comprises a closure adapted to engage with and seal the sample container, and wherein the device is supplied with a quantity of preservative solution for preserving excised sample held within the sample container, such that the tip of the punch is immersed in the preservative solution, and wherein the seal prevents leakage of the preservation solution from the sample container.

2. A device as claimed in claim 1, wherein the closure is attached to or integral with the sample collector such that, when the closure is in sealing engagement with the sample container, the sample collector is contained inside the sample container.

3. A device as claimed in claim 2, wherein a sample cutter is disposed at the distal end of the punch.

4. A device as claimed in claim 3, wherein the sample cutter comprises at least one cutting member extending across the distal end of the punch.

5. A device as claimed in claim 4, wherein there are provided at least two cutting members extending across the distal end of the punch.

6. A device as claimed in claim 4, wherein the at least one cutting member is a wire.

7. A device as claimed in claim 5, wherein the cutting members form a cross in the distal end of the punch.

8. A device as claimed in claim 1, wherein the punch is provided with at least one lateral opening via which sample preservative can pass into the channel and hence come into contact with a sample held in that channel.

9. A device as claimed in claim 8, wherein said at least one lateral opening is smaller than the opening in the sample collector through which the sample enters the sample collector.

10. A method for obtaining a biological sample from a subject, the method comprising the steps of:
    a) contacting a sample collector of the device according to claim 1 with a subject such that the sample cutter cuts into the subject;
    b) withdrawing the sample collector from the subject such that a biological sample is excised from the subject; and
    c) inserting the sample collector into sample container, such that the excised sample is preserved by sample preservative.

11. The method according to claim 10, wherein the subject is a dead human, or part thereof.

* * * * *